US012642842B2

(12) United States Patent
Pons

(10) Patent No.: US 12,642,842 B2
(45) Date of Patent: Jun. 2, 2026

(54) THERAPEUTIC AND COSMETIC USES OF BOTULINUM NEUROTOXIN SEROTYPE E

(71) Applicant: IPSEN BIOPHARM LIMITED, Wrexham (GB)

(72) Inventor: Laurent Pons, Wrexham (GB)

(73) Assignee: Ipsen Biopharm Limited, Wrexham (GB)

( * ) Notice: Subject to any disclaimer, the term of this patent is extended or adjusted under 35 U.S.C. 154(b) by 702 days.

(21) Appl. No.: 17/278,545

(22) PCT Filed: Jul. 4, 2019

(86) PCT No.: PCT/GB2019/051902
§ 371 (c)(1),
(2) Date: Mar. 22, 2021

(87) PCT Pub. No.: WO2020/065249
PCT Pub. Date: Apr. 2, 2020

(65) Prior Publication Data
US 2021/0353725 A1 Nov. 18, 2021

(30) Foreign Application Priority Data
Sep. 28, 2018 (GB) ..................................... 1815844

(51) Int. Cl.
A61K 38/48 (2006.01)
A61K 8/66 (2006.01)
A61Q 19/00 (2006.01)

(52) U.S. Cl.
CPC ........... *A61K 38/4893* (2013.01); *A61K 8/66* (2013.01); *A61Q 19/00* (2013.01); *C12Y 304/24069* (2013.01)

(58) Field of Classification Search
None
See application file for complete search history.

(56) References Cited

U.S. PATENT DOCUMENTS 6,967,088 B1 * 11/2005 Williams ............. C07K 14/245
435/71.1
7,132,259 B1 11/2006 Dolly et al.
(Continued)

FOREIGN PATENT DOCUMENTS

EP 1206554 B2 10/2010
EP 2272340 A1 1/2011
(Continued)

OTHER PUBLICATIONS

Neagu, Tiberiu Paul; et al; "The Benefits of Botulinum Neurotoxin Treatments in a Multitude of Medical Conditions" Rev Chim, 68, 2978-2983, 2017 (Year: 2017).*
(Continued)

*Primary Examiner* — David W Berke-Schlessel
(74) *Attorney, Agent, or Firm* — Proskauer Rose LLP

(57) ABSTRACT

A botulinum neurotoxin serotype E (BoNT/E) for use in treating a disorder or a cosmetic condition, wherein the BoNT/E provides a maximum inhibition of neurotransmitter secretion from a target cell or tissue 13 days or less after administration to a human subject and the inhibition is reduced but is greater than 25% at day 14 following administration. A method for treating a disorder or a cosmetic condition, the method comprising administering the aforementioned BoNT/E.

24 Claims, 13 Drawing Sheets

Specification includes a Sequence Listing.

(56)                    References Cited

U.S. PATENT DOCUMENTS

| 7,226,605 | B2 | 6/2007 | Suskind et al. |
| 7,825,233 | B2* | 11/2010 | Steward ................. C07K 14/33 |
| | | | 536/23.7 |
| 8,003,601 | B2 | 8/2011 | Frevert et al. |
| 8,071,110 | B2 | 12/2011 | Steward et al. |
| 2005/0074466 | A1 | 4/2005 | Suskind et al. |
| 2005/0220734 | A1 | 10/2005 | First |
| 2007/0166332 | A1 | 7/2007 | Steward et al. |
| 2009/0004225 | A1 | 1/2009 | Fernandez-Salas et al. |
| 2009/0202591 | A1 | 8/2009 | Steward et al. |
| 2011/0318385 | A1 | 12/2011 | Jackson et al. |
| 2015/0174217 | A1 | 6/2015 | Dolly et al. |
| 2019/0183987 | A1 | 6/2019 | Abushakra et al. |
| 2019/0185523 | A1 | 6/2019 | Jacky et al. |
| 2019/0185837 | A1 | 6/2019 | Jacky et al. |
| 2019/0343759 | A1 | 11/2019 | Steward et al. |
| 2020/0383894 | A1 | 12/2020 | Pickett et al. |
| 2023/0225954 | A1 | 7/2023 | Axen et al. |
| 2024/0016718 | A1 | 1/2024 | Maignel et al. |
| 2024/0175001 | A1 | 5/2024 | Liu et al. |
| 2024/0327472 | A1 | 10/2024 | Moore et al. |

FOREIGN PATENT DOCUMENTS

| JP | 2004538310 | A | 12/2004 |
| JP | 2019520799 | A | 7/2019 |
| WO | 200208268 | A2 | 1/2002 |
| WO | 2002044199 | A2 | 6/2002 |
| WO | 02/089834 | A1 | 11/2002 |
| WO | 03011333 | A1 | 2/2003 |
| WO | 2006027207 | A1 | 3/2006 |
| WO | 2006094539 | A1 | 9/2006 |
| WO | 2006114308 | A2 | 11/2006 |
| WO | 2007104567 | A2 | 9/2007 |
| WO | 2010094905 | A1 | 8/2010 |
| WO | 2010120766 | A1 | 10/2010 |
| WO | 2013/068476 | A1 | 5/2013 |
| WO | 2014/068317 | A1 | 5/2014 |
| WO | 2015/188944 | A1 | 12/2015 |
| WO | 2015188945 | A1 | 12/2015 |
| WO | 2017191315 | A1 | 11/2017 |
| WO | 2018009903 | A2 | 1/2018 |
| WO | 2018/175688 | A1 | 9/2018 |
| WO | 2018/195435 | A1 | 10/2018 |
| WO | 2019122166 | A1 | 6/2019 |
| WO | 2020020878 | A1 | 1/2020 |
| WO | 2020065249 | A1 | 4/2020 |
| WO | 2021152328 | A1 | 8/2021 |

OTHER PUBLICATIONS

Eleopra, Roberto; et al; "Different time courses of recovery after poisoning with botulinum neurotoxin serotypes A and E in humans" Neuroscience Letters, 256, 135-138, 1998 (Year: 1998).*

Earp, Ana Paula de Sa; Marmur, Ellen S; "The five D's of botulinum toxin: Doses, dilution, diffusion, duration and dogma" Journal of Cosmetic and Laser Therapy, 10, 93-102, 2008 (Year: 2008).*

Slawek et al., Neurological Sciences (2005), 26:32-39.

Chen et al., Toxins (2012), 4:1196-1222.

International Search Report, issued Nov. 4, 2019, in PCT/GB2019/051902.

International Search Report for PCT/GB2021/050215 dated Apr. 22, 2021 (5 pages).

Ahrens, Jamie M., et al., "Differential activity of 2-methylene-19-nor vitamin D analogs on growth factor gene expression in rhino mouse skin and comparison to all-trans retinoic acid", PLoS One, vol. 12, No. 11, Nov. 2017, Article ID e0188887, DOI: 10.1371/journal.pone.0188887 (20 pages).

Benavides, Fernando, et al., "The hairless mouse in skin research", J Dermatol Sci., vol. 53, No. 1, Jan. 2009 (Epub Oct. 2008), pp. 10-18, DOI: 10.1016/j.jdermsci.2008.08.012, Author Manuscript (19 pages).

Brennan, Connie, "Botulinum Toxin Type-A (BONT-A) Injections of the Corrugator Muscles for Aesthetics and Depression?", Plast Surg Nurs., vol. 36, No. 4, Oct./Dec. 2016, pp. 167-169, DOI: 10.1097/PSN.0000000000000159 (3 pages).

Campanati, Anna, et al., "Botulinum Toxin Off-Label Use in Dermatology: A Review", Skin Appendage Disord., vol. 3, No. 1, Mar. 2017, pp. 39-56, DOI: 10.1159/000452341 (18 pages).

Gazerani, P., et al., "Botulinum toxin type A reduces histamine-induced itch and vasomotor responses in human skin", Br J Dermatol., vol. 161, No. 4, Oct. 2009, pp. 737-745, DOI: 10.1111/j.1365-2133.2009.09305.x (9 pages).

Grando, S. A., et al., "The non-neuronal and nonmuscular effects of botulinum toxin: An opportunity for a deadly molecule to treat disease in the skin and beyond", Br J Dermatol., vol. 178, No. 5, May 2018, pp. 1011-1019, DOI: 10.1111/bjd. 16080 (9 pages).

Gritsanenko, M. G., et al., "Botulotoxin, Applications and Effects on Humans", Abstract [in Russian w/ English Translation], Successes of Modern Natural Science, No. 9, 2013, pp. 117-118 (4 pages).

Gugerell, Alfred, et al., "Botulinum Toxin A: Dose-dependent Effect on Reepithelialization and Angiogenesis", Plast Reconstr Surg Glob Open, vol. 4, No. 8, Aug. 2016, Article ID e837, DOI: 10.1097/GOX.0000000000000852 (7 pages).

Han, Sang Bum, et al., "Protective Effect of Botulinum Toxin Type A Against Atopic Dermatitis-Like Skin Lesions in NC/Nga Mice", Dermatol Surg., vol. 43, Suppl. 3, Dec. 2017, pp. S312-S321, DOI: 10.1097/DSS.0000000000001170 (10 pages).

Hinde, Eleanor, et al., "A practical guide for the study of human and murine sebaceous glands in situ", Exp Dermatol., vol. 22, No. 10, Oct. 2013, pp. 631-637, DOI: 10.1111/exd.12207 (7 pages).

Hsia, Edward, et al., "Effects of topically applied acitretin in reconstructed human epidermis and the rhino mouse", J Invest Dermatol., vol. 128, No. 1, Jan. 2008 (Epub Jul. 2007), pp. 125-130, DOI: 10.1038/sj.jid.5700968 (6 pages).

Jakubke, H.-D, et al., "Amino Acids, Peptides, Proteins", Textbook [in Russian w/ English translation], translated from German by N. P. Zapevalova and E. E. Maksimova, Ed. Yu. V. Mitin, Moscow: Mir Publishers, 1985, pp. 92-94 (11 pages).

Kawaji, Hisanori, "Rhino Mouse", Experimental Animals [In Japanese w/ English Abs.], vol. 23, No. 2, 1974, pp. 43-58, DOI: 10.1538/expanim1957.23.2_43 (16 pages).

Kendall, Alexandra C., et al., "Lipidomics for translational skin research: A primer for the uninitiated", Exp Dermatol., vol. 27, No. 7, Jul. 2018, pp. 721-728, DOI: 10.1111/exd.13558 (8 pages).

Kharkevich, D. A., "Pharmacology [Farmakologiya]", Textbook [in Russian w/ English Translation], 10th Ed., Moscow: GEOTAR-Media, 2010, pp. 73-74 (8 pages).

Kim, Min Jung, et al., "Assessment of Skin Physiology Change and Safety After Intradermal Injections With Botulinum Toxin: A Randomized, Double-Blind, Placebo-Controlled, Split-Face Pilot Study in Rosacea Patients With Facial Erythema", Dermatol Surg., vol. 45, No. 9, Sep. 2019, pp. 1155-1162, DOI: 10.1097/DSS.0000000000001819 (8 pages).

Kligman, Lorraine H., et al., "The effect on rhino mouse skin of agents which influence keratinization and exfoliation", J Invest Dermatol., vol. 73, No. 5, Nov. 1979, pp. 354-358, DOI: 10.1111/1523-1747.ep12550409 (5 pages).

Li, Shan, et al., "Lipidomic analysis of epidermal lipids: A tool to predict progression of inflammatory skin disease in humans", Expert Rev Proteomics, vol. 13, No. 5, May 2016, pp. 451-456, DOI: 10.1080/14789450.2016.1177462 (7 pages).

Li, Zheng Jun, et al., "Regulation of lipid production by acetylcholine signalling in human sebaceous glands", J Dermatol Sci., vol. 72, No. 2, Nov. 2013, pp. 116-122, DOI: 10.1016/j.jdermsci.2013.06.009 (7 pages).

Mashkovsky, M. D., "Medicinal Products: A Guide for Physicians", In 2 Volumes, vol. 1: 14th Ed., revised, corrected, and supplemented, Moscow, New Wave Publishing House LLC, S.B. Divov, 2002, pp. 8-9 [in Russian w/ English Translation], ISBN: 5-7864-0128-6 (15 pages).

Min, Peiru, et al., "Sebum Production Alteration after Botulinum Toxin Type A Injections for the Treatment of Forehead Rhytides: A Prospective Randomized Double-Blind Dose-Comparative Clinical

(56)　　　　　References Cited

OTHER PUBLICATIONS

Investigation", Aesthet Surg J., vol. 35, No. 5, Jul. 2015, pp. 600-610, DOI: 10.1093/asj/sju150 (11 pages).

Mizukawa, R., et al., "Atopic Dermatitis—Its Relationship with Systemic Diseases", Kyorin Medical Journal [in Japanese w/ English Translation], vol. 49, No. 2, 2018, pp. 159-161, DOI: 10.11434/kyorinmed.49.159 (7 pages).

Nicolaides, N., et al., "Lipid compsition on comedones compared with that of human skin surface in acne patients", J Invest Dermatol., vol. 54, No. 6, Jun. 1970, pp. 487-495, DOI: 10.1111/1523-1747. ep12259307 (9 pages).

Odorisio, Teresa, et al., "The atypical retinoid E-3-(3'-Adamantan-1-yl-4'-methoxybiphenyl-4-yl)-2-propenoic acid (ST1898) displays comedolytic activity in the rhino mouse model", Eur J Dermatol., vol. 22, No. 4, Jul.-Aug. 2012, pp. 505-511, DOI: 10.1684/ejd.2012. 1778 (7 pages).

Picardo, Mauro, et al., "Sebaceous gland lipids", Dermatoendocrinol., vol. 1, No. 2, Mar. 2009, pp. 68-71, DOI: 10.4161/derm. 1.2.8472 (5 pages).

Ramezanli, Tannaz, et al., "Development and Characterization of a Topical Gel Formulation of Adapalene-TyroSpheres and Assessment of Its Clinical Efficacy", Mol Pharm., vol. 15, No. 9, Sep. 2018, pp. 3813-3822, DOI: 10.1021/acs.molpharmaceut.8b00318 (10 pages).

Rose, Amy E., et al., "Safety and efficacy of intradermal injection of botulinum toxin for the treatment of oily skin", Dermatol Surg., vol. 39, No. 3 Part 1, Mar. 2013, pp. 443-448, DOI: 10.1111/dsu. 12097 (6 pages).

Sapra, Priya, et al., "A Single-blind, Split-face, Randomized, Pilot Study Comparing the Effects of Intradermal and Intramuscular Injection of Two Commercially Available Botulinum Toxin A Formulas to Reduce Signs of Facial Aging", J Clin Aesthet Dermatol., vol. 10, No. 2, Feb. 2017, pp. 34-44, PMID: 28367260 (11 pages).

Sayed, Khadiga S., et al., "The efficacy of intradermal injections of botulinum toxin in the management of enlarged facial pores and seborrhea: A split face-controlled study", J Dermatolog Treat., vol. 32, No. 7, Nov. 2021 (Epub 2020), pp. 771-777, DOI: 10.1080/09546634.2019.1708241 (8 pages).

Scaglione, Francesco, "Conversion Ratio between Botox®, Dysport®, and Xeomin® in Clinical Practice", Toxins (Basel), vol. 8, No. 3, Mar. 2016, Article ID 65, DOI: 10.3390/toxins8030065 (10 pages).

Seiberg, Miri, et al., "The effects of trypsin on apoptosis, utriculi size, and skin elasticity in the Rhino mouse", J Invest Dermatol., vol. 109, No. 3, Sep. 1997, pp. 370-376, DOI: 0.1111/1523-1747. ep12336244 (7 pages).

Shah, Anil R., "Use of intradermal botulinum toxin to reduce sebum production and facial pore size", J Drugs Dermatol., vol. 7, No. 9, Sep. 2008, pp. 847-850, PMID: 19112798 (4 pages).

Smith, K. R., et al., "[Thematic Review Series: Skin Lipids] Sebaceous Gland Lipids: Friend or Foe?", J Lipid Res., vol. 49, No. 2, Feb. 2008 (Epub Nov. 2007), pp. 271-281, DOI: 10.1194/jlr. R700015-JLR200 (11 pages).

Summerfield, Artur, et al., "The immunology of the porcine skin and its value as a model for human skin", Mol Immunol., vol. 66, No. 1, Jul. 2015 (Epub Nov. 2014), pp. 14-21, DOI: 10.1016/j.molimm. 2014.10.023 (8 pages).

Ward, Nicole L., et al., "Botulinum neurotoxin A decreases infiltrating cutaneous lymphocytes and improves acanthosis in the KC-Tie2 mouse model", J Invest Dermatol., vol. 132, No. 7, Jul. 2012, pp. 1927-1930, DOI: 10.1038/jid.2012.60 (4 pages).

Zouboulis, Christos C., et al., "Frontiers in sebaceous gland biology and pathology", Exp Dermatol., vol. 17, No. 6, Jun. 2008, pp. 542-551, DOI: 10.1111/j.1600-0625.2008.00725.x (10 pages).

* cited by examiner

Extensor digitorum brevis rBoNT-E time course of effect (mean ± s.e.m.)
EXTENSOR DIGITORUM BREVIS Dysport time course of effect (mean ± s.e.m.)
EXTENSOR DIGITORUM BREVIS rBoNT-E time course of effect (mean ± s.e.m.)
EXTENSOR DIGITORUM BREVIS rBoNT-E time course of effect (mean ± s.e.m.)
EXTENSOR DIGITORUM BREVIS Dysport time course of effect (mean ± s.e.m.)
EXTENSOR DIGITORUM BREVIS Comparative Effects on CMAP inhibition (mean ± s.e.m.)
EXTENSOR DIGITORUM BREVIS Comparative Effects on CMAP inhibition (mean ± s.e.m.)
EXTENSOR DIGITORUM BREVIS rBoNT-E time course effect (mean +/- s.e.m)
EXTENSOR DIGITORIUM BREVIS
(9 CBA units – 3.6 ng)

SEQUENCE LISTING

```
<160> NUMBER OF SEQ ID NOS: 5

<210> SEQ ID NO 1
<211> LENGTH: 3759
<212> TYPE: DNA
<213> ORGANISM: Artificial Sequence
<220> FEATURE:
<223> OTHER INFORMATION: Synthetic

<400> SEQUENCE: 1
atgccaaaaa ttaatagttt taattataat gatcctgtta atgatagaac aattttatat      60
attaaaccag gcggttgtca agaattttat aaatcattta atattatgaa aaatatttgg     120
ataattccag agagaaatgt aattggtaca acccccaag attttcatcc gcctacttca      180
ttaaaaaatg gagatagtag ttattatgac cctaattatt tacaaagtga tgaagaaaag     240
gatagatttt taaaaatagt cacaaaaata tttaatagaa taaataataa tctttcagga     300
gggattttat tagaagaact gtcaaaagct aatccatatt tagggaatga taatactcca     360
gataatcaat tccatattgg tgatgcatca gcagttgaga ttaaattctc aaatggtagc     420
caagacatac tattacctaa tgttattata atgggagcag agcctgattt atttgaaact     480
aacagttcca atatttctct aagaaataat tatatgccaa gcaatcacgg ttttggatca     540
atagctatag taacattctc acctgaatat tcttttagat ttaatgataa tagtatgaat     600
gaatttattc aagatcctgc tcttacatta atgcatgaat taatacattc attacatgga     660
ctatatgggg ctaaagggat tactacaaag tatactataa cacaaaaaca aaatccccta     720
ataacaaata taagaggtac aaatattgaa gaattcttaa cttttggagg tactgattta     780
aacattatta ctagtgctca gtccaatgat atctatacta atcttctagc tgattataaa     840
aaaatagcgt ctaaacttag caaagtacaa gtatctaatc cactacttaa tccttataaa     900
gatgtttttg aagcaaagta tggattagat aaagatgcta gcggaattta ttcggtaaat     960
ataaacaaat ttaatgatat ttttaaaaaa ttatacagct ttacggaatt tgatttagca    1020
actaaatttc aagttaaatg taggcaaact tatattggac agtataaata cttcaaactt    1080
tcaaacttgt aaatgattc tatttataat atatcagaag gctataatat aaataattta    1140
aaggtaaatt ttagaggaca gaatgcaaat ttaaatccta gaattattac accaattaca    1200
ggtagaggac tagtaaaaaa aatcattaga ttttgtaaaa atattgtttc tgtaaaaggc    1260
ataaggaaat caatatgtat cgaaataaat aatggtgagt tatttttgt ggcttccgag    1320 aatagttata atgatgataa tataaatact cctaaagaaa ttgacgatac agtaacttca    1380
aataataatt atgaaaatga tttagatcag gttattttaa attttaatag tgaatcagca    1440
cctggacttt cagatgaaaa attaaattta actatccaaa atgatgctta tacccaaaaa    1500
tatgattcta tggaacaag tgatatagaa caacatgatg ttaatgaact taatgtattt    1560
ttctatttag atgcacagaa agtgcccgaa ggtgaaaata atgtcaatct cacctcttca    1620
attgatacag cattattaga acaacctaaa atatatacat tttttcatc agaatttatt    1680
```

-continued

```
aataatgtca ataaacctgt gcaagcagca ttatttgtaa gctggataca acaagtgtta      1740
gtagatttta ctactgaagc taaccaaaaa agtactgttg ataaaattgc agatatttct      1800
atagttgttc catatatagg tcttgcttta aatataggaa atgaagcaca aaaaggaaat      1860
tttaaagatg cacttgaatt attaggagca ggtatttat  tagaatttga acccgagctt      1920
ttaattccta caatttttagt attcacgata aaatctttt  taggttcatc tgataataaa      1980
aataaagtta ttaaagcaat aaataatgca ttgaaagaaa gagatgaaaa atggaaagaa      2040
gtatatagtt ttatagtatc gaattggatg actaaaatta atacacaatt taataaaaga      2100
aaagaacaaa tgtatcaagc tttacaaaat caagtaaatg caattaaaac aataatagaa      2160
tctaagtata atagttatac tttagaggaa aaaaatgagc ttacaaataa atatgatatt      2220
aagcaaatag aaaatgaact taatcaaaag gtttctatag caatgaataa tatagacagg      2280
ttcttaactg aaagttctat atcctattta atgaaattaa taaatgaagt aaaaattaat      2340
aaattaagag aatatgatga gaatgtcaaa acgtatttat tgaattatat tatacaacat      2400
ggatcaatct tgggagagag tcagcaagaa ctaaattcta tggtaactga taccctaaat      2460
aatagtattc cttttaagct ttcttcttat acagatgata aaattttaat ttcatatttt      2520
aataaattct ttaagagaat taaaagtagt tcagtttttaa atatgagata taaaaatgat      2580
aaatacgtag atacttcagg atatgattca aatataaata ttaatggaga tgtatataaa      2640
tatccaacta ataaaaatca atttggaata tataatgata aacttagtga agttaatata      2700
tctcaaaatg attacattat atatgataat aaatataaaa attttagtat tagttttttgg      2760 gtaagaattc ctaactatga taataagata gtaaatgtta ataatgaata cactataata      2820
aattgtatga gagataataa ttcaggatgg aaagtatctc ttaatcataa tgaaataatt      2880
tggacattgc aagataatgc aggaattaat caaaaattag catttaacta tggtaacgca      2940
aatggtattt ctgattatat aaataagtgg attttttgtaa ctataactaa tgatagatta      3000
ggagattcta aactttatat taatggaaat ttaatagatc aaaaatcaat tttaaattta      3060
ggtaatattc atgttagtga caatatatta tttaaaatag ttaattgtag ttatacaaga      3120
tatattggta ttagatattt taatattttt gataaagaat tagatgaaac agaaattcaa      3180
actttatata gcaatgaacc taatacaaat attttgaagg attttttgggg aaattatttg      3240 ctttatgaca agaatacta  tttattaaat gtgttaaaac caaataactt tattgatagg      3300
agaaaagatt ctactttaag cattaataat ataagaagca ctattcttt  agctaataga      3360 ttatatagtg gaataaaagt taaaatacaa agagttaata atagtagtac taacgataat      3420
cttgttagaa agaatgatca ggtatatatt aattttgtag ccagcaaaac tcacttattt      3480
ccattatatg ctgatacagc taccacaaat aaagagaaaa caataaaaat atcatcatct      3540
ggcaatagat ttaatcaagt agtagttatg aattcagtag gaaataattg tacaatgaat      3600
tttaaaaata ataatggaaa taatattggg ttgttaggtt tcaaggcaga tactgtagtt      3660
gctagtactt ggtattatac acatatgaga gatcatacaa acagcaatgg atgtttttgg      3720
aactttattt ctgaagaaca tggatggcaa gaaaaataa                            3759
```

<210> SEQ ID NO 2
<211> LENGTH: 1251
<212> TYPE: PRT
<213> ORGANISM: Clostridium botulinum

<400> SEQUENCE: 2

Pro Lys Ile Asn Ser Phe Asn Tyr Asn Asp Pro Val Asn Asp Arg Thr

-continued

```
1                5                    10                   15

Ile Leu Tyr Ile Lys Pro Gly Gly Cys Gln Glu Phe Tyr Lys Ser Phe
             20              25              30

Asn Ile Met Lys Asn Ile Trp Ile Ile Pro Glu Arg Asn Val Ile Gly
             35              40              45

Thr Thr Pro Gln Asp Phe His Pro Pro Thr Ser Leu Lys Asn Gly Asp
    50              55              60

Ser Ser Tyr Tyr Asp Pro Asn Tyr Leu Gln Ser Asp Glu Glu Lys Asp
65              70              75              80

Arg Phe Leu Lys Ile Val Thr Lys Ile Phe Asn Arg Ile Asn Asn Asn
             85              90              95

Leu Ser Gly Gly Ile Leu Leu Glu Glu Leu Ser Lys Ala Asn Pro Tyr
             100             105             110

Leu Gly Asn Asp Asn Thr Pro Asp Asn Gln Phe His Ile Gly Asp Ala
             115             120             125

Ser Ala Val Glu Ile Lys Phe Ser Asn Gly Ser Gln Asp Ile Leu Leu
    130             135             140

Pro Asn Val Ile Ile Met Gly Ala Glu Pro Asp Leu Phe Glu Thr Asn
145             150             155             160

Ser Ser Asn Ile Ser Leu Arg Asn Asn Tyr Met Pro Ser Asn His Gly
             165             170             175

Phe Gly Ser Ile Ala Ile Val Thr Phe Ser Pro Glu Tyr Ser Phe Arg
             180             185             190

Phe Asn Asp Asn Ser Met Asn Glu Phe Ile Gln Asp Pro Ala Leu Thr
             195             200             205

Leu Met His Glu Leu Ile His Ser Leu His Gly Leu Tyr Gly Ala Lys
    210             215             220

Gly Ile Thr Thr Lys Tyr Thr Ile Thr Gln Lys Gln Asn Pro Leu Ile
225             230             235             240

Thr Asn Ile Arg Gly Thr Asn Ile Glu Glu Phe Leu Thr Phe Gly Gly
             245             250             255

Thr Asp Leu Asn Ile Ile Thr Ser Ala Gln Ser Asn Asp Ile Tyr Thr
             260             265             270

Asn Leu Leu Ala Asp Tyr Lys Lys Ile Ala Ser Lys Leu Ser Lys Val
             275             280             285

Gln Val Ser Asn Pro Leu Leu Asn Pro Tyr Lys Asp Val Phe Glu Ala
    290             295             300

Lys Tyr Gly Leu Asp Lys Asp Ala Ser Gly Ile Tyr Ser Val Asn Ile
305             310             315             320

Asn Lys Phe Asn Asp Ile Phe Lys Lys Leu Tyr Ser Phe Thr Glu Phe
             325             330             335

Asp Leu Ala Thr Lys Phe Gln Val Lys Cys Arg Gln Thr Tyr Ile Gly
             340             345             350

Gln Tyr Lys Tyr Phe Lys Leu Ser Asn Leu Leu Asn Asp Ser Ile Tyr
             355             360             365

Asn Ile Ser Glu Gly Tyr Asn Ile Asn Asn Leu Lys Val Asn Phe Arg
    370             375             380

Gly Gln Asn Ala Asn Leu Asn Pro Arg Ile Ile Thr Pro Ile Thr Gly
385             390             395             400

Arg Gly Leu Val Lys Lys Ile Ile Arg Phe Cys Lys Asn Ile Val Ser
             405             410             415

Val Lys Gly Ile Arg Lys Ser Ile Cys Ile Glu Ile Asn Asn Gly Glu
             420             425             430
```

-continued

```
Leu Phe Phe Val Ala Ser Glu Asn Ser Tyr Asn Asp Asp Asn Ile Asn
        435                 440                 445

Thr Pro Lys Glu Ile Asp Asp Thr Val Thr Ser Asn Asn Asn Tyr Glu
        450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
                485                 490                 495

Ile Pro Lys Tyr Asp Ser Asn Gly Thr Ser Asp Ile Glu Gln His Asp
                500                 505                 510

Val Asn Glu Leu Asn Val Phe Phe Tyr Leu Asp Ala Gln Lys Val Pro
        515                 520                 525

Glu Gly Glu Asn Asn Val Asn Leu Thr Ser Ser Ile Asp Thr Ala Leu
        530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Ser Trp Ile Gln
                565                 570                 575

Gln Val Leu Val Asp Phe Thr Thr Glu Ala Asn Gln Lys Ser Thr Val
        580                 585                 590

Asp Lys Ile Ala Asp Ile Ser Ile Val Val Pro Tyr Ile Gly Leu Ala
        595                 600                 605

Leu Asn Ile Gly Asn Glu Ala Gln Lys Gly Asn Phe Lys Asp Ala Leu
        610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
                645                 650                 655

Asp Asn Lys Asn Lys Val Ile Lys Ala Ile Asn Asn Ala Leu Lys Glu
                660                 665                 670

Arg Asp Glu Lys Trp Lys Glu Val Tyr Ser Phe Ile Val Ser Asn Trp
        675                 680                 685

Met Thr Lys Ile Asn Thr Gln Phe Asn Lys Arg Lys Glu Gln Met Tyr
        690                 695                 700

Gln Ala Leu Gln Asn Gln Val Asn Ala Ile Lys Thr Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Lys Gln Ile Glu Asn Glu Leu Asn Gln Lys Val Ser Ile
                740                 745                 750

Ala Met Asn Asn Ile Asp Arg Phe Leu Thr Glu Ser Ser Ile Ser Tyr
        755                 760                 765

Leu Met Lys Leu Ile Asn Glu Val Lys Ile Asn Lys Leu Arg Glu Tyr
        770                 775                 780

Asp Glu Asn Val Lys Thr Tyr Leu Leu Asn Tyr Ile Ile Gln His Gly
785                 790                 795                 800

Ser Ile Leu Gly Glu Ser Gln Gln Glu Leu Asn Ser Met Val Thr Asp
                805                 810                 815

Thr Leu Asn Asn Ser Ile Pro Phe Lys Leu Ser Ser Tyr Thr Asp Asp
                820                 825                 830

Lys Ile Leu Ile Ser Tyr Phe Asn Lys Phe Phe Lys Arg Ile Lys Ser
        835                 840                 845
```

-continued

```
Ser Ser Val Leu Asn Met Arg Tyr Lys Asn Asp Lys Tyr Val Asp Thr
850             855             860

Ser Gly Tyr Asp Ser Asn Ile Asn Ile Asn Gly Asp Val Tyr Lys Tyr
865             870             875             880

Pro Thr Asn Lys Asn Gln Phe Gly Ile Tyr Asn Asp Lys Leu Ser Glu
                885             890             895

Val Asn Ile Ser Gln Asn Asp Tyr Ile Ile Tyr Asp Asn Lys Tyr Lys
            900             905             910

Asn Phe Ser Ile Ser Phe Trp Val Arg Ile Pro Asn Tyr Asp Asn Lys
            915             920             925

Ile Val Asn Val Asn Asn Glu Tyr Thr Ile Ile Asn Cys Met Arg Asp
    930             935             940

Asn Asn Ser Gly Trp Lys Val Ser Leu Asn His Asn Glu Ile Ile Trp
945             950             955             960

Thr Leu Gln Asp Asn Ala Gly Ile Asn Gln Lys Leu Ala Phe Asn Tyr
                965             970             975

Gly Asn Ala Asn Gly Ile Ser Asp Tyr Ile Asn Lys Trp Ile Phe Val
                980             985             990

Thr Ile Thr Asn Asp Arg Leu Gly  Asp Ser Lys Leu Tyr  Ile Asn Gly
        995             1000             1005

Asn Leu  Ile Asp Gln Lys Ser  Ile Leu Asn Leu Gly  Asn Ile His
    1010             1015             1020

Val Ser  Asp Asn Ile Leu Phe  Lys Ile Val Asn Cys  Ser Tyr Thr
    1025             1030             1035

Arg Tyr  Ile Gly Ile Arg Tyr  Phe Asn Ile Phe Asp  Lys Glu Leu
    1040             1045             1050

Asp Glu  Thr Glu Ile Gln Thr  Leu Tyr Ser Asn Glu  Pro Asn Thr
    1055             1060             1065

Asn Ile  Leu Lys Asp Phe Trp  Gly Asn Tyr Leu Leu  Tyr Asp Lys
    1070             1075             1080

Glu Tyr  Tyr Leu Leu Asn Val  Leu Lys Pro Asn Asn  Phe Ile Asp
    1085             1090             1095

Arg Arg  Lys Asp Ser Thr Leu  Ser Ile Asn Asn Ile  Arg Ser Thr
    1100             1105             1110

Ile Leu  Leu Ala Asn Arg Leu  Tyr Ser Gly Ile Lys  Val Lys Ile
    1115             1120             1125

Gln Arg  Val Asn Asn Ser Ser  Thr Asn Asp Asn Leu  Val Arg Lys
    1130             1135             1140

Asn Asp  Gln Val Tyr Ile Asn  Phe Val Ala Ser Lys  Thr His Leu
    1145             1150             1155

Phe Pro  Leu Tyr Ala Asp Thr  Ala Thr Thr Asn Lys  Glu Lys Thr
    1160             1165             1170

Ile Lys  Ile Ser Ser Ser Gly  Asn Arg Phe Asn Gln  Val Val Val
    1175             1180             1185

Met Asn  Ser Val Gly Asn Asn  Cys Thr Met Asn Phe  Lys Asn Asn
    1190             1195             1200

Asn Gly  Asn Asn Ile Gly Leu  Leu Gly Phe Lys Ala  Asp Thr Val
    1205             1210             1215

Val Ala  Ser Thr Trp Tyr Tyr  Thr His Met Arg Asp  His Thr Asn
    1220             1225             1230

Ser Asn  Gly Cys Phe Trp Asn  Phe Ile Ser Glu Glu  His Gly Trp
    1235             1240             1245

Gln Glu  Lys
```

-continued

```
        1250

<210> SEQ ID NO 3
<211> LENGTH: 1251
<212> TYPE: PRT
<213> ORGANISM: Clostridium botulinum

<400> SEQUENCE: 3

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln Asp Ile Leu
        130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
            195                 200                 205

Thr Leu Met His Glu Leu Ile His Ser Leu His Gly Leu Tyr Gly Ala
        210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
        290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Arg Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365
```

-continued

```
Tyr Asn Ile Ser Glu Gly Tyr Asn Ile Asn Asn Leu Lys Val Asn Phe
    370             375                 380

Arg Gly Gln Asn Ala Asn Leu Asn Pro Arg Ile Ile Thr Pro Ile Thr
385                 390             395                 400

Gly Arg Gly Leu Val Lys Lys Ile Ile Arg Phe Cys Lys Asn Ile Val
            405             410             415

Ser Val Lys Gly Ile Arg Lys Ser Ile Cys Ile Glu Ile Asn Asn Gly
            420             425             430

Glu Leu Phe Phe Val Ala Ser Glu Asn Ser Tyr Asn Asp Asp Asn Ile
        435             440             445

Asn Thr Pro Lys Glu Ile Asp Asp Thr Val Thr Ser Asn Asn Asn Tyr
    450             455             460

Glu Asn Asp Leu Asp Gln Val Ile Leu Asn Phe Asn Ser Glu Ser Ala
465             470             475             480

Pro Gly Leu Ser Asp Glu Lys Leu Asn Leu Thr Ile Gln Asn Asp Ala
            485             490             495

Tyr Ile Pro Lys Tyr Asp Ser Asn Gly Thr Ser Asp Ile Glu Gln His
            500             505             510

Asp Val Asn Glu Leu Asn Val Phe Phe Tyr Leu Asp Ala Gln Lys Val
            515             520             525

Pro Glu Gly Glu Asn Asn Val Asn Leu Thr Ser Ser Ile Asp Thr Ala
    530             535             540

Leu Leu Glu Gln Pro Lys Ile Tyr Thr Phe Phe Ser Ser Glu Phe Ile
545             550             555             560

Asn Asn Val Asn Lys Pro Val Gln Ala Ala Leu Phe Val Ser Trp Ile
            565             570             575

Gln Gln Val Leu Val Asp Phe Thr Thr Glu Ala Asn Gln Lys Ser Thr
            580             585             590

Val Asp Lys Ile Ala Asp Ile Ser Ile Val Val Pro Tyr Ile Gly Leu
            595             600             605

Ala Leu Asn Ile Gly Asn Glu Ala Gln Lys Gly Asn Phe Lys Asp Ala
        610             615             620

Leu Glu Leu Leu Gly Ala Gly Ile Leu Leu Glu Phe Glu Pro Glu Leu
625             630             635             640

Leu Ile Pro Thr Ile Leu Val Phe Thr Ile Lys Ser Phe Leu Gly Ser
            645             650             655

Ser Asp Asn Lys Asn Lys Val Ile Lys Ala Ile Asn Asn Ala Leu Lys
            660             665             670

Glu Arg Asp Glu Lys Trp Lys Glu Val Tyr Ser Phe Ile Val Ser Asn
        675             680             685

Trp Met Thr Lys Ile Asn Thr Gln Phe Asn Lys Arg Lys Glu Gln Met
    690             695             700

Tyr Gln Ala Leu Gln Asn Gln Val Asn Ala Ile Lys Thr Ile Ile Glu
705             710             715             720

Ser Lys Tyr Asn Ser Tyr Thr Leu Glu Glu Lys Asn Glu Leu Thr Asn
            725             730             735

Lys Tyr Asp Ile Lys Gln Ile Glu Asn Glu Leu Asn Gln Lys Val Ser
            740             745             750

Ile Ala Met Asn Asn Ile Asp Arg Phe Leu Thr Glu Ser Ser Ile Ser
            755             760             765

Tyr Leu Met Lys Ile Ile Asn Glu Val Lys Ile Asn Lys Leu Arg Glu
    770             775             780

Tyr Asp Glu Asn Val Lys Thr Tyr Leu Leu Asn Tyr Ile Ile Gln His
```

-continued

```
785               790               795               800

Gly Ser Ile Leu Gly Glu Ser Gln Gln Glu Leu Asn Ser Met Val Thr
                805               810               815

Asp Thr Leu Asn Asn Ser Ile Pro Phe Lys Leu Ser Ser Tyr Thr Asp
                820               825               830

Asp Lys Ile Leu Ile Ser Tyr Phe Asn Lys Phe Phe Lys Arg Ile Lys
                835               840               845

Ser Ser Ser Val Leu Asn Met Arg Tyr Lys Asn Asp Lys Tyr Val Asp
850               855               860

Thr Ser Gly Tyr Asp Ser Asn Ile Asn Ile Asn Gly Asp Val Tyr Lys
865               870               875               880

Tyr Pro Thr Asn Lys Asn Gln Phe Gly Ile Tyr Asn Asp Lys Leu Ser
                885               890               895

Glu Val Asn Ile Ser Gln Asn Asp Tyr Ile Ile Tyr Asp Asn Lys Tyr
                900               905               910

Lys Asn Phe Ser Ile Ser Phe Trp Val Arg Ile Pro Asn Tyr Asp Asn
                915               920               925

Lys Ile Val Asn Val Asn Asn Glu Tyr Thr Ile Ile Asn Cys Met Arg
930               935               940

Asp Asn Asn Ser Gly Trp Lys Val Ser Leu Asn His Asn Glu Ile Ile
945               950               955               960

Trp Thr Phe Glu Asp Asn Arg Gly Ile Asn Gln Lys Leu Ala Phe Asn
                965               970               975

Tyr Gly Asn Ala Asn Gly Ile Ser Asp Tyr Ile Asn Lys Trp Ile Phe
                980               985               990

Val Thr Ile Thr Asn Asp Arg Leu  Gly Asp Ser Lys Leu  Tyr Ile Asn
        995               1000               1005

Gly Asn  Leu Ile Asp Gln Lys  Ser Ile Leu Asn Leu  Gly Asn Ile
    1010               1015               1020

His Val  Ser Asp Asn Ile Leu  Phe Lys Ile Val Asn  Cys Ser Tyr
    1025               1030               1035

Thr Arg  Tyr Ile Gly Ile Arg  Tyr Phe Asn Ile Phe  Asp Lys Glu
    1040               1045               1050

Leu Asp  Glu Thr Glu Ile Gln  Thr Leu Tyr Ser Asn  Glu Pro Asn
    1055               1060               1065

Thr Asn  Ile Leu Lys Asp Phe  Trp Gly Asn Tyr Leu  Leu Tyr Asp
    1070               1075               1080

Lys Glu  Tyr Tyr Leu Leu Asn  Val Leu Lys Pro Asn  Asn Phe Ile
    1085               1090               1095

Asp Arg  Arg Lys Asp Ser Thr  Leu Ser Ile Asn Asn  Ile Arg Ser
    1100               1105               1110

Thr Ile  Leu Leu Ala Asn Arg  Leu Tyr Ser Gly Ile  Lys Val Lys
    1115               1120               1125

Ile Gln  Arg Val Asn Asn Ser  Ser Thr Asn Asp Asn  Leu Val Arg
    1130               1135               1140

Lys Asn  Asp Gln Val Tyr Ile  Asn Phe Val Ala Ser  Lys Thr His
    1145               1150               1155

Leu Phe  Pro Leu Tyr Ala Asp  Thr Ala Thr Thr Asn  Lys Glu Lys
    1160               1165               1170

Thr Ile  Lys Ile Ser Ser Ser  Gly Asn Arg Phe Asn  Gln Val Val
    1175               1180               1185

Val Met  Asn Ser Val Gly Asn  Cys Thr Met Asn Phe  Lys Asn Asn
    1190               1195               1200
```

```
Asn Gly  Asn Asn Ile Gly Leu  Leu Gly Phe Lys Ala  Asp Thr Val
    1205             1210              1215

Val Ala  Ser Thr Trp Tyr Tyr  Thr His Met Arg Asp  His Thr Asn
    1220             1225              1230

Ser Asn  Gly Cys Phe Trp Asn  Phe Ile Ser Glu Glu  His Gly Trp
    1235             1240              1245

Gln Glu  Lys
    1250

<210> SEQ ID NO 4
<211> LENGTH: 421
<212> TYPE: PRT
<213> ORGANISM: Clostridium botulinum

<400> SEQUENCE: 4

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Pro Thr Ser Leu Lys Asn Gly Asp
    50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln Asp Ile Leu Leu
    130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
            165                 170                 175

Phe Gly Ser Ile Ala Ile Val Thr Phe Ser Pro Glu Tyr Ser Phe Arg
            180                 185                 190

Phe Asn Asp Asn Ser Met Asn Glu Phe Ile Gln Asp Pro Ala Leu Thr
        195                 200                 205

Leu Met His Glu Leu Ile His Ser Leu His Gly Leu Tyr Gly Ala Lys
    210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
        275                 280                 285

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
```

-continued

```
305                310                315                320

Asn Lys Phe Asn Asp Ile Phe Lys Lys Leu Tyr Ser Phe Thr Glu Phe
              325                330                335

Asp Leu Ala Thr Lys Phe Gln Val Lys Cys Arg Gln Thr Tyr Ile Gly
              340                345                350

Gln Tyr Lys Tyr Phe Lys Leu Ser Asn Leu Leu Asn Asp Ser Ile Tyr
              355                360                365

Asn Ile Ser Glu Gly Tyr Asn Ile Asn Asn Leu Lys Val Asn Phe Arg
              370                375                380

Gly Gln Asn Ala Asn Leu Asn Pro Arg Ile Ile Thr Pro Ile Thr Gly
385                390                395                400

Arg Gly Leu Val Lys Lys Ile Ile Arg Phe Cys Lys Asn Ile Val Ser
              405                410                415

Val Lys Gly Ile Arg
              420

<210> SEQ ID NO 5
<211> LENGTH: 830
<212> TYPE: PRT
<213> ORGANISM: Clostridium botulinum

<400> SEQUENCE: 5

Lys Ser Ile Cys Ile Glu Ile Asn Asn Gly Glu Leu Phe Phe Val Ala
1                5                10                15

Ser Glu Asn Ser Tyr Asn Asp Asp Asn Ile Asn Thr Pro Lys Glu Ile
              20                25                30

Asp Asp Thr Val Thr Ser Asn Asn Asn Tyr Glu Asn Asp Leu Asp Gln
              35                40                45

Val Ile Leu Asn Phe Asn Ser Glu Ser Ala Pro Gly Leu Ser Asp Glu
              50                55                60

Lys Leu Asn Leu Thr Ile Gln Asn Asp Ala Tyr Ile Pro Lys Tyr Asp
65                70                75                80

Ser Asn Gly Thr Ser Asp Ile Glu Gln His Asp Val Asn Glu Leu Asn
              85                90                95

Val Phe Phe Tyr Leu Asp Ala Gln Lys Val Pro Glu Gly Glu Asn Asn
              100                105                110

Val Asn Leu Thr Ser Ser Ile Asp Thr Ala Leu Leu Glu Gln Pro Lys
              115                120                125

Ile Tyr Thr Phe Phe Ser Ser Glu Phe Ile Asn Asn Val Asn Lys Pro
              130                135                140

Val Gln Ala Ala Leu Phe Val Ser Trp Ile Gln Gln Val Leu Val Asp
145                150                155                160

Phe Thr Thr Glu Ala Asn Gln Lys Ser Thr Val Asp Lys Ile Ala Asp
              165                170                175

Ile Ser Ile Val Val Pro Tyr Ile Gly Leu Ala Leu Asn Ile Gly Asn
              180                185                190

Glu Ala Gln Lys Gly Asn Phe Lys Asp Ala Leu Glu Leu Leu Gly Ala
              195                200                205

Gly Ile Leu Leu Glu Phe Glu Pro Glu Leu Leu Ile Pro Thr Ile Leu
              210                215                220

Val Phe Thr Ile Lys Ser Phe Leu Gly Ser Ser Asp Asn Lys Asn Lys
225                230                235                240

Val Ile Lys Ala Ile Asn Asn Ala Leu Lys Glu Arg Asp Glu Lys Trp
              245                250                255
```

-continued

```
Lys Glu Val Tyr Ser Phe Ile Val Ser Asn Trp Met Thr Lys Ile Asn
            260                 265                 270

Thr Gln Phe Asn Lys Arg Lys Glu Gln Met Tyr Gln Ala Leu Gln Asn
            275                 280                 285

Gln Val Asn Ala Ile Lys Thr Ile Ile Glu Ser Lys Tyr Asn Ser Tyr
        290                 295                 300

Thr Leu Glu Glu Lys Asn Glu Leu Thr Asn Lys Tyr Asp Ile Lys Gln
305                 310                 315                 320

Ile Glu Asn Glu Leu Asn Gln Lys Val Ser Ile Ala Met Asn Asn Ile
                325                 330                 335

Asp Arg Phe Leu Thr Glu Ser Ser Ile Ser Tyr Leu Met Lys Leu Ile
            340                 345                 350

Asn Glu Val Lys Ile Asn Lys Leu Arg Glu Tyr Asp Glu Asn Val Lys
            355                 360                 365

Thr Tyr Leu Leu Asn Tyr Ile Ile Gln His Gly Ser Ile Leu Gly Glu
        370                 375                 380

Ser Gln Gln Glu Leu Asn Ser Met Val Thr Asp Thr Leu Asn Asn Ser
385                 390                 395                 400

Ile Pro Phe Lys Leu Ser Ser Tyr Thr Asp Asp Lys Ile Leu Ile Ser
                405                 410                 415

Tyr Phe Asn Lys Phe Phe Lys Arg Ile Lys Ser Ser Ser Val Leu Asn
            420                 425                 430

Met Arg Tyr Lys Asn Asp Lys Tyr Val Asp Thr Ser Gly Tyr Asp Ser
            435                 440                 445

Asn Ile Asn Ile Asn Gly Asp Val Tyr Lys Tyr Pro Thr Asn Lys Asn
        450                 455                 460

Gln Phe Gly Ile Tyr Asn Asp Lys Leu Ser Glu Val Asn Ile Ser Gln
465                 470                 475                 480

Asn Asp Tyr Ile Ile Tyr Asp Asn Lys Tyr Lys Asn Phe Ser Ile Ser
                485                 490                 495

Phe Trp Val Arg Ile Pro Asn Tyr Asp Asn Lys Ile Val Asn Val Asn
            500                 505                 510

Asn Glu Tyr Thr Ile Ile Asn Cys Met Arg Asp Asn Asn Ser Gly Trp
            515                 520                 525

Lys Val Ser Leu Asn His Asn Glu Ile Ile Trp Thr Leu Gln Asp Asn
        530                 535                 540

Ala Gly Ile Asn Gln Lys Leu Ala Phe Asn Tyr Gly Asn Ala Asn Gly
545                 550                 555                 560

Ile Ser Asp Tyr Ile Asn Lys Trp Ile Phe Val Thr Ile Thr Asn Asp
                565                 570                 575

Arg Leu Gly Asp Ser Lys Leu Tyr Ile Asn Gly Asn Leu Ile Asp Gln
            580                 585                 590

Lys Ser Ile Leu Asn Leu Gly Asn Ile His Val Ser Asp Asn Ile Leu
            595                 600                 605

Phe Lys Ile Val Asn Cys Ser Tyr Thr Arg Tyr Ile Gly Ile Arg Tyr
        610                 615                 620

Phe Asn Ile Phe Asp Lys Glu Leu Asp Glu Thr Glu Ile Gln Thr Leu
625                 630                 635                 640

Tyr Ser Asn Glu Pro Asn Thr Asn Ile Leu Lys Asp Phe Trp Gly Asn
                645                 650                 655

Tyr Leu Leu Tyr Asp Lys Glu Tyr Tyr Leu Leu Asn Val Leu Lys Pro
            660                 665                 670

Asn Asn Phe Ile Asp Arg Arg Lys Asp Ser Thr Leu Ser Ile Asn Asn
```

-continued

```
        675                 680                 685

Ile Arg Ser Thr Ile Leu Leu Ala Asn Arg Leu Tyr Ser Gly Ile Lys
    690                 695                 700

Val Lys Ile Gln Arg Val Asn Asn Ser Ser Thr Asn Asp Asn Leu Val
705                 710                 715                 720

Arg Lys Asn Asp Gln Val Tyr Ile Asn Phe Val Ala Ser Lys Thr His
                725                 730                 735

Leu Phe Pro Leu Tyr Ala Asp Thr Ala Thr Thr Asn Lys Glu Lys Thr
            740                 745                 750

Ile Lys Ile Ser Ser Ser Gly Asn Arg Phe Asn Gln Val Val Val Met
        755                 760                 765

Asn Ser Val Gly Asn Asn Cys Thr Met Asn Phe Lys Asn Asn Asn Gly
    770                 775                 780

Asn Asn Ile Gly Leu Leu Gly Phe Lys Ala Asp Thr Val Val Ala Ser
785                 790                 795                 800

Thr Trp Tyr Tyr Thr His Met Arg Asp His Thr Asn Ser Asn Gly Cys
                805                 810                 815

Phe Trp Asn Phe Ile Ser Glu Glu His Gly Trp Gln Glu Lys
                820                 825                 830
```

THERAPEUTIC AND COSMETIC USES OF BOTULINUM NEUROTOXIN SEROTYPE E

This application is a national stage of International Patent Application No. PCT/GB2019/051902, filed Jul. 4, 2019, which claims the priority benefit of British Application No. 1815844.4, filed Sep. 28, 2018.

The present invention relates to clostridial neurotoxins and therapeutic and cosmetic uses thereof.

Bacteria in the genus Clostridia produce highly potent and specific protein toxins, which can poison neurons and other cells to which they are delivered. Examples of such clostridial toxins include the neurotoxins produced by *C. tetani* (TeNT) and by *C. botulinum* (BoNT) serotypes A-G, and X (see WO 2018/009903 A2), as well as those produced by *C. baratii* and *C. butyricum*.

Among the clostridial neurotoxins are some of the most potent toxins known. By way of example, botulinum neurotoxins have median lethal dose ($LD_{50}$) values for mice ranging from 0.5 to 5 ng/kg, depending on the serotype. Both tetanus and botulinum toxins act by inhibiting the function of affected neurons, specifically the release of neurotransmitters. While botulinum toxin acts at the neuromuscular junction and inhibits cholinergic transmission in the peripheral nervous system, tetanus toxin acts in the central nervous system.

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the translocation domain components. Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of clostridial neurotoxins are non-cytotoxic proteases that cleave SNARE proteins.

Botulinum neurotoxins are well known for their ability to cause a flaccid muscle paralysis. Said muscle-relaxant properties have led to botulinum neurotoxins (such as BoNT/A) being employed in a variety of medical and cosmetic procedures, including treatment of glabellar lines or hyperkinetic facial lines, headache, hemifacial spasm, hyperactivity of the bladder, hyperhidrosis, nasal labial lines, cervical dystonia, blepharospasm, and spasticity.

However, BoNT/A is associated with a long duration of effect (e.g. >6 months), which is disadvantageous in certain therapeutic or cosmetic situations. Thus, there remains a need for an alternative therapeutic having different pharmacodynamic properties to BoNT/A.

The present invention overcomes one or more of the above-mentioned problems.

The present inventors are the first to determine the pharmacodynamic properties of BoNT/E (e.g. BoNT/E lacking any complexing proteins that are present in naturally occurring BoNT/E) when administered to a human subject. Surprisingly, the inventors have found that BoNT/E has different pharmacodynamic properties to BoNT/A, including a short time to achieve maximal inhibition of neurotransmitter release from a target cell or tissue, and a short duration of effect (e.g. <150 days from administration).

Although BoNT/E has been tested in in vitro systems and non-human animal models (such as mice), previous studies performed with naturally-occurring complexed BoNT/E are not suitable for predicting the pharmacodynamic properties of uncomplexed (e.g. recombinant) BoNT/E as these distinct forms of BoNT are known to behave differently in vivo. For example, the complexed and uncomplexed forms of BoNTs demonstrate a significantly different host cell response in human neural cells.

Based on the findings of the present inventors, suitable BoNT/E clinical utilities can be determined for achieving a therapeutic effect in a human subject.

Thus, in one aspect the present invention provides a botulinum neurotoxin serotype E (BoNT/E) for use in treating a disorder. Related aspects include a method for treating a disorder, and use of a BoNT/E in the manufacture of a medicament for treating a disorder, wherein the BoNT/E is administered to a human subject.

In one aspect there is provided a botulinum neurotoxin serotype E (BoNT/E) for use in treating a disorder, wherein the BoNT/E is administered to a human subject, and provides a maximum inhibition of neurotransmitter secretion from a target cell or tissue ≤13 in days after administration; and (wherein the inhibition of neurotransmitter secretion) reduces to >25% inhibition of neurotransmitter secretion from the target cell or tissue at day 14 after administration.

Another aspect provides a method for treating a disorder, the method comprising administering a BoNT/E to a human subject, and wherein the administering a BoNT/E provides a maximum inhibition of neurotransmitter secretion from a target cell or tissue in ≤13 days after administration; and (wherein the inhibition of neurotransmitter secretion) reduces to >25% inhibition of neurotransmitter secretion from the target cell or tissue at day 14 after administration.

A further aspect provides a cosmetic method comprising administering a BoNT/E to a human subject, wherein the administering a BoNT/E provides a maximum inhibition of neurotransmitter secretion from a target cell or tissue in ≤13 days after administration; and (wherein the inhibition of neurotransmitter secretion) reduces to >25% inhibition of neurotransmitter secretion from the target cell or tissue at day 14 after administration.

A yet further aspect provides use of a BoNT/E in the manufacture of a medicament for treating a disorder, wherein the BoNT/E is administered to a human subject and provides a maximum inhibition of neurotransmitter secretion from a target cell or tissue ≤13 in days after administration; and (wherein the inhibition of neurotransmitter secretion) reduces to >25% inhibition of neurotransmitter secretion from the target cell or tissue at day 14 after administration.

The BoNT/E is preferably in a non-complexed form (i.e. free from complexing proteins that are present in naturally occurring BoNT/E). Examples of such complexing proteins include a neurotoxin-associated proteins (NAP) and a non-toxic-nonhemagglutinin component (NTNH).

One advantage of a BoNT/E in a non-complexed form is that the total weight by protein content is provided by the neurotoxin (BoNT/E) per se. Thus, administration of e.g. 5 ng of a BoNT/E in a non-complexed form typically corresponds to an administration of 5 ng of BoNT/E neurotoxin. In contrast, administration of e.g. 5 ng of BoNT/E in a complexed form (preferably where the total weight by protein content is determined by absorbance at A280, or e.g. a Bradford Assay) will include complexing protein(s) and will result in a reduced (i.e. less than 5 ng) administration amount of BoNT/E.

BoNT/E in a non-complexed form (as described above) typically contains less than 50 picograms (pg) complex protein per 100 nanograms (ng) of BoNT/E protein; for example, less than 20 pg complex protein per 100 ng of BoNT/E protein. In one embodiment, BoNT/E in a non-complexed form contains less than 10 pg complex protein per 100 ng of BoNT/E protein, for example less than 5 pg complex protein per 100 ng of BoNT/E protein.

The BoNT/E of the present invention is preferably recombinant BoNT/E (and thus free from complex proteins).

The term "treat" or "treating" as used herein encompasses prophylactic treatment (e.g. to prevent onset of a disease) as well as corrective treatment (treatment of a subject already suffering from a disease). Preferably "treat" or "treating" as used herein means corrective treatment. The term "treat" or "treating" encompasses treating both the disease and a symptom thereof. In some embodiments "treat" or "treating" refers to a symptom of a disease.

Therefore, a BoNT/E may be administered to a human subject in a therapeutically effective amount or a prophylactically effective amount.

A "therapeutically effective amount" is any amount of the BoNT/E, which when administered alone or in combination to a human subject for treating a disease (or a symptom thereof) is sufficient to effect such treatment of the disease, or symptom thereof.

A "prophylactically effective amount" is any amount of the BoNT/E that, when administered alone or in combination to a human subject inhibits or delays the onset or reoccurrence of a disease (or a symptom thereof). In some embodiments, the prophylactically effective amount prevents the onset or reoccurrence of a disease entirely. "Inhibiting" the onset means either lessening the likelihood of disease onset (or symptom thereof), or preventing the onset entirely.

The term "inhibition of neurotransmitter release from a tissue" may mean inhibition of neurotransmitter release from a nerve within said tissue.

The present invention additionally provides a cosmetic method comprising administering a BoNT/E to a human subject.

BoNT/E may be administered to a human subject in any manner suitable to achieve the desired therapeutic effect. In one embodiment, BoNT/E is administered parenterally. Such administration may be via localised injection. In one embodiment, BoNT/E is administered by subcutaneous injection, intradermal injection and/or intramuscular injection. Preferably BoNT/E is administered intramuscularly, e.g. by intramuscular injection.

The total dose of BoNT/E administered to a human subject is typically not less than 0.03 ng and typically not more than 50 ng. For example, in some embodiment the total dose of BoNT/E administered is approximately 5, 6, 7, 8, 9, 10, 11, 12, 13, 14, 15, 20, 25, 30, 40 or 50 ng.

The term "total dose" means the absolute quantity (expressed in grams or nanograms) of BoNT/E administered to a patient per treatment regimen. For example, reference a total dose of BoNT/E of 5 ng means that 5 ng of BoNT/E is administered to a human patient and completes the treatment regimen for that patient.

The total dose may be administered by way of one or more administration step forming part of the same treatment regimen. For example, a total dose of 5 ng may be administered by a first administration of 2 ng BoNT/E, and second administration of 3 ng BoNT/E.

Preferably, the total dose is administered in a single administration step.

The total dose of BoNT/E administered is typically less than 50 ng, such as less than 40, 30, 20 or 10 ng.

One advantage of the present invention is that it provides a rapid onset of action (e.g. inhibition of neurotransmitter release). This is highly desirable for many clinical and cosmetic indications. A separate advantage of the present invention is that local diffusion of BoNT/E to adjacent muscles is substantially avoided (i.e. no noticeable effect is observed).

Thus, according to the present invention, BoNT/E is administered and (e.g at a dose that) provides at least 15% inhibition of neurotransmitter secretion from a target cell or tissue in 1 day or less, preferably in less than 15 hours, after administration. For example, BoNT/E is administered and (e.g. at a dose that) provides at least 20% inhibition of neurotransmitter secretion from a target cell or tissue in 1 day or less, preferably in less than 15 hours, after administration.

In one embodiment BoNT/E is administered and (e.g. at a dose that) provides >20%, >30%, >40%, >50%, >60%, >70%, or >80% inhibition of neurotransmitter secretion from the target cell or tissue at day 14 after administration. For example, BoNT/E is preferably administered and (e.g. at a dose that) provides >25% inhibition of neurotransmitter secretion from the target cell or tissue at day 14 after administration. BoNT/E may be administered and (e.g. at a dose that) provides >25% inhibition of neurotransmitter secretion from the target cell or tissue at day 14-49 after administration.

In another embodiment BoNT/E is administered and (e.g. at a dose that) provides 40-95% inhibition of neurotransmitter secretion from a target cell or tissue in ≤13, ≤12, ≤11, ≤10, ≤9, ≤8 or ≤7 days after administration. For example, BoNT/E is administered and (e.g. at a dose that) provides 40-60% inhibition of neurotransmitter secretion from a target cell or tissue in ≤13, ≤12, ≤11, ≤10, ≤9, ≤8, or ≤7 days after administration.

In one embodiment BoNT/E is administered and (e.g. at a dose that) provides 40-95% inhibition of neurotransmitter secretion from a target cell or tissue in ≤6 days after administration. For example, BoNT/E is administered and (e.g. at a dose that) provides 40-60% inhibition of neurotransmitter secretion from a target cell or tissue in ≤6 days after administration.

In another embodiment BoNT/E is administered to a human subject and (e.g. at a dose that) provides at least 40% inhibition of neurotransmitter secretion from the target cell or tissue in ≤13 days from administration, preferably days. For example, BoNT/E is administered to a human subject and (e.g. at a dose that) provides at least 50% inhibition of neurotransmitter secretion from the target cell or tissue in ≤13 days from administration, preferably ≤6 days.

In one embodiment, BoNT/E is administered and (e.g. at a dose that) provides a maximum inhibition of neurotransmitter secretion from a target cell or tissue in 15 days or less, preferably in 10 days or less, more preferably in 7 days or less after administration.

A further advantage of the present invention is that it also provides a fast off-set (i.e. following maximum inhibition of neurotransmitter secretion from a target cell or tissue) relative to BoNT/A of action. This is highly desirable for many clinical indications.

According to the present invention, BoNT/E is administered and (e.g. at a dose that) provides:

at least 40% inhibition of neurotransmitter secretion from a target cell or tissue in ≤13 (preferably ≤12 or ≤10) days after administration; and reduces to 15% or less inhibition of neurotransmitter secretion from the target cell or tissue in >21 to <100 days after administration.

For example, BoNT/E is administered and (e.g. at a dose that) provides:

at least 40% inhibition of neurotransmitter secretion from a target cell or tissue in ≤13 days after administration; and reduces to 15% or less inhibition of neurotransmitter secretion from the target cell or tissue in >21 to <80 days after administration.

In one embodiment, BoNT/E is administered and (e.g. at a dose that) provides:

at least 40% inhibition of neurotransmitter secretion from a target cell or tissue in ≤13 days after administration; and reduces to 15% or less inhibition of neurotransmitter secretion from the target cell or tissue in >40 to <100 days after administration.

For example, BoNT/E is administered to a human subject and (e.g. at a dose that) provides: at least 40% inhibition of neurotransmitter secretion from a target cell or tissue in (preferably ≤12 or ≤10) days after administration; and reduces to 15% or less inhibition of neurotransmitter secretion from the target cell or tissue in >40 to <80 days after administration.

The inhibition of neurotransmitter secretion from a target cell or tissue (preferably from a target tissue) may be assessed by routine techniques known to the person skilled in the art.

In one embodiment "% inhibition of neurotransmitter secretion" as used herein corresponds to the % inhibition of a muscle action potential (e.g. a compound muscle action potential, CMAP). Inhibition of a muscle action potential may be assessed using standard techniques. For example, the action potential of a stimulated muscle may be measured prior to and after BoNT/E administration by way of electrodes to determine the % inhibition. For example, electrodes may be used in electrophysiological studies for measuring an action potential (caused due to neurotransmitter secretion) within a tissue, and determining the % inhibition of action potential (corresponding to % inhibition of neurotransmitter release).

Thus, in one embodiment, % inhibition of neurotransmitter secretion from a target cell or tissue is measured by means of electrophysiology. For example, % inhibition of an action potential (measured by electrophysiology) may be measured, providing a readout of % inhibition of neurotransmitter secretion.

A key advantage of using electrophysiology to measure % inhibition of neurotransmitter secretion is that a standardised approach may be taken, with the provision of objective results. This contrasts with subjective methods of measuring % inhibition of neurotransmitter secretion, such as by inferring % inhibition based on manual/human (e.g. medical practitioner) assessment of a response to treatment, such as manual assessment of the level of muscle spasticity, or facial wrinkling, subsequent to treatment. The results of such subjective methods are often subject to a high degree of variability, and thus lack to precision and reliability of objective methods.

The "% inhibition of neurotransmitter secretion" may correspond to a % inhibition measured at a superficial tissue being particularly accessible for electrophysiology studies, for example the Extensor Digitorum Brevis (EDB) muscle. By measuring % inhibition of neurotransmitter secretion at such a superficial tissue, a more accurate/reliable readout (compared with measurement at a less superficial tissue) may be provided, which may advantageously be extrapolated to % inhibition of neurotransmitter secretion at an alternative tissue (targeted for therapeutic or cosmetic purposes).

An assessment of said "% inhibition of neurotransmitter secretion" is demonstrated by reference to the accompanying Examples and Materials and Methods, and may be assessed using the methodology described therein (e.g. the Pharmacodynamic Model described therein).

In one embodiment the neurotransmitter is acetylcholine.

The present inventors have found that a BoNT/E may be administered and (e.g. at a dose that) provides a rapid onset of inhibition of neurotransmitter secretion, and a subsequent gradual (substantially linear) recovery of neurotransmitter secretion (subsequent to maximum inhibition). Such gradual recovery may advantageously be dose-independent, and has been demonstrated by the present inventors for doses in the range of 0.04 ng to approx. 4.0 ng.

Thus, the present invention advantageously provides a total dose of BoNT/E that provides a predictable, substantially linear decrease in "% inhibition of neurotransmitter secretion" (subsequent to maximal inhibition) in a human subject, such that the subject's response to treatment may be predicted for up to 100 days subsequent to administration (see FIG. 12). For example, where the BoNT/E suppresses a symptom of a disorder, it may be predicted at which time point a symptom may begin to recur, together with predicting the severity of a recurring symptom at a given time point.

Thus, in one embodiment BoNT/E is administered and (e.g. at a dose) provides substantially linear decrease in "% inhibition of neurotransmitter secretion" subsequent to maximal inhibition.

The term "substantially linear" means that a profile (plot) of values of "% inhibition of neurotransmitter secretion" may be fit with a linear curve (Microsoft Excel 2010, Microsoft Corporation) having an R-squared value of >0.8. In one embodiment, said R-squared value is >0.85, >0.9, or >0.95. Preferably, said R-squared value may be >0.9. More preferably, said R-squared value may be >0.95.

In one embodiment, BoNT/E is administered and (e.g. at a dose that) provides a substantially linear decrease in "% inhibition of neurotransmitter secretion" subsequent to maximal inhibition, wherein said substantially linear decrease is over days 10-56, 10-42 and/or days 10-21 after administration.

Preferably, said profile over days 10-56, 10-42 and/or days 10-21 after administration represents an "offset" of the BoNT/E effect (inhibition of neurotransmitter secretion) subsequent to maximum inhibition of neurotransmitter secretion.

In one embodiment BoNT/E is administered and (e.g. at a dose that) provides maximal inhibition of neurotransmitter secretion from a target cell or tissue in ≤13, ≤12, ≤11, ≤10, ≤9, 8≤, ≤7, or ≤6 days (preferably days) after administration, and a subsequent reduction in the % inhibition of neurotransmitter secretion from a target cell or tissue of 1-10% per day.

Said maximum inhibition (% inhibition of neurotransmitter secretion) may ≥40%, ≥60%, ≥75%, or ≥80% (for example, ≥85%). Preferably, said maximum inhibition is >80%.

In one embodiment, said maximum inhibition (% inhibition of neurotransmitter secretion) is ≥95%.

The % inhibition of neurotransmitter secretion from a target cell or tissue typically reduces by about 2-10% per day per day subsequent to maximum inhibition.

For example, the % inhibition of neurotransmitter secretion from a target cell or tissue reduces by about 1-4%, about 4-6%, about 6-8%, or about 8-10% per day for each day subsequent to maximum inhibition. Preferably, the % inhibition of neurotransmitter secretion from a target cell or tissue reduces by about 1-4% for each day subsequent to maximum inhibition The % inhibition of neurotransmitter secretion from a target cell or tissue typically reduces by about 1-4% each day from day 10-21, from day 6-42, from day 10-42, from day 10-49 and/or from day 10-56 after administration.

For convenience, the reduction in % inhibition of neurotransmitter secretion may be calculated as an average reduction across the timeframe in question, for example from day 10-24, from day 6-42, from day 10-42, from day 10-49 and/or from day 10-56 after administration.

The % inhibition of neurotransmitter secretion from a target cell or tissue may reduce by about 1-30% per week for each week subsequent to maximum inhibition. For example, the % inhibition of neurotransmitter secretion from a target cell or tissue reduces by about 1-28%, 2-28%, about 2-22%, about 4-16%, about 9-18%, about 14-16% or about 9-12% per week for each week subsequent to maximum inhibition.

In one embodiment, the % inhibition of neurotransmitter secretion from a target cell or tissue reduces by about 9-17% each week from week 1-3, week 1-6, and/or from week 2-6 after administration.

For convenience, the reduction in % inhibition of neurotransmitter secretion may be calculated as an average reduction across the timeframe in question, for example from week 1-6, from week 2-6, and/or week 1-3 after administration.

Said maximum inhibition (% inhibition of neurotransmitter secretion) may ≥40%, ≥60%, ≥75%, or ≥80% (for example, ≥85%). Preferably, said maximum inhibition is >80%.

In one embodiment, said maximum inhibition (% inhibition of neurotransmitter secretion) is ≥95%.

The % inhibition of neurotransmitter secretion may plateau after said substantially linear decrease in "% inhibition of neurotransmitter secretion".

In one embodiment BoNT/E is administered and (e.g. at a dose that) provides between about 10%-40% (preferably about 15%-40%) inhibition of neurotransmitter secretion from the target cell or tissue between >49 to <100 days, or >49 to <90 days after administration. In one embodiment BoNT/E is administered and (e.g. at a dose that) provides between about 10%-40% (preferably about 15%-40%) inhibition of neurotransmitter secretion from the target cell or tissue between >42 to <100 days, or >42 to <90 days after administration.

In use, the total dose of BoNT/E administered is typically less than 10 ng, for example in the range of 0.04 to 5 ng. In one embodiment, BoNT/E is administered at a dose of 0.5-5 ng (e.g. 0.9 ng or 3.6 ng). In another embodiment BoNT/E is administered at a dose of 0.1-0.5 ng (e.g. 0.2 ng). In one embodiment BoNT/E is administered at a dose of 1-5 ng (e.g. 3.6 ng). In another embodiment BoNT/E is administered at a dose of 0.5-2 ng (e.g. 0.9 ng).

In one embodiment BoNT/E is administered at a dose of 0.5-5 ng (e.g. 0.9 ng or 3.6 ng) that provides:
at least 85% inhibition of neurotransmitter secretion from a target cell or tissue at 7 days after administration; and/or
at least 80% inhibition of neurotransmitter secretion from a target cell or tissue at 14 days after administration; and/or
at least 70% inhibition of neurotransmitter secretion from a target cell or tissue at 21 days after administration; and/or
at least 50% inhibition of neurotransmitter secretion from a target cell or tissue at 28 days after administration; and/or
at least 40% inhibition of neurotransmitter secretion from a target cell or tissue at 35 days after administration; and/or
at least 30% inhibition of neurotransmitter secretion from a target cell or tissue at 42 days after administration; and/or
at least 25% inhibition of neurotransmitter secretion from a target cell or tissue at 49 days after administration.

For example, BoNT/E is administered at a dose of 0.5-5 ng (e.g. 0.9 ng or 3.6 ng) that provides:
at least 15% inhibition of neurotransmitter secretion from a target cell or tissue at 56 days after administration; and/or
≤15% inhibition of neurotransmitter secretion from a target cell or tissue in at 63 days after administration.

In another embodiment BoNT/E is administered at a dose of 0.1-0.5 ng (e.g. 0.2 ng) that provides:
at least 65% inhibition of neurotransmitter secretion from a target cell or tissue at 7 days after administration; and/or
at least 65% inhibition of neurotransmitter secretion from a target cell or tissue at 14 days after administration; and/or
at least 50% inhibition of neurotransmitter secretion from a target cell or tissue at 21 days after administration; and/or
at least 30% inhibition of neurotransmitter secretion from a target cell or tissue at 28 days after administration; and/or
at least 30% inhibition of neurotransmitter secretion from a target cell or tissue at 35 days after administration; and/or
≤15% inhibition of neurotransmitter secretion from a target cell or tissue at 42 days after administration.

In one embodiment BoNT/E is administered at a dose of 1-5 ng (e.g. 3.6 ng) that provides:
at least 85% inhibition of neurotransmitter secretion from a target cell or tissue between about >3 to ≤13 days after administration; and/or

between about 80%-90% (preferably about 84%-86%) inhibition of neurotransmitter secretion from the target cell or tissue between >17 to <19 days after administration; and/or between about 70%-80% (preferably about 74%-76%) inhibition of neurotransmitter secretion from the target cell or tissue between >20 to <22 days after administration; and/or between about 55%-65% (preferably about 60%-64%) inhibition of neurotransmitter secretion from the target cell or tissue between >23 to <26 days after administration; and/or between about 50%-60% (preferably about 54%-56%) inhibition of neurotransmitter secretion from the target cell or tissue between >27 to <29 days after administration; and/or between about 35%-45% (preferably about 43%-44%) inhibition of neurotransmitter secretion from the target cell or tissue between >34 to <36 days after administration; and/or between about 30%-40% (preferably about 34%-36%) inhibition of neurotransmitter secretion from the target cell or tissue between >41 to <43 days after administration; and/or between about 25%-35% (preferably about 29%-31%) inhibition of neurotransmitter secretion from the target cell or tissue between >48 to <50 days after administration; and/or between about 10%-20% (preferably about 15%-17%) inhibition of neurotransmitter secretion from the target cell or tissue between >55 to <57 days after administration; and/or between about 7%-17% (preferably about 13%-15%) inhibition of neurotransmitter secretion from the target cell or tissue between >62 to <64 days after administration; and/or ≤15% inhibition of neurotransmitter secretion from the target cell or tissue in >75 days after administration.

In another embodiment BoNT/E is administered at a dose of 0.5-2 ng (e.g. 0.9 ng) that provides:

at least 85% inhibition of neurotransmitter secretion from a target cell or tissue between >3 to ≤13 days after administration; and/or between about 70%-80% (preferably about 77%-79%) inhibition of neurotransmitter secretion from the target cell or tissue between >17 to <19 days after administration; and/or between about 65%-75% (preferably about 71%-73%) inhibition of neurotransmitter secretion from the target cell or tissue between >20 to <22 days after administration; and/or between about 60%-70% (preferably about 65%-67%) inhibition of neurotransmitter secretion from the target cell or tissue between >23 to <26 days after administration; and/or between about 55%-65% (preferably about 58%-60%) inhibition of neurotransmitter secretion from the target cell or tissue between >27 to <29 days after administration; and/or between about 45%-55% (preferably about 50%-52%) inhibition of neurotransmitter secretion from the target cell or tissue between >34 to <36 days after administration; and/or between about 30%-40% (preferably about 34%-37%) inhibition of neurotransmitter secretion from the target cell or tissue between >41 to <43 days after administration; and/or

between about 30%-40% (preferably about 33%-35% inhibition of neurotransmitter secretion from the target cell or tissue between >48 to <50 days after administration; and/or between about 30%-40% (preferably about 35%-37%) inhibition of neurotransmitter secretion from the target cell or tissue between >55 to <57 days after administration; and/or between about 20%-30% (preferably about 22%-27%) inhibition of neurotransmitter secretion from the target cell or tissue between >62 to <64 days after administration; and/or ≤15% inhibition of neurotransmitter secretion from the target cell or tissue in >75 days (e.g. >85 days) after administration.

In one embodiment BoNT/E is administered at a dose of 0.1-0.5 ng (e.g. 0.2 ng) that provides:

at least 70% inhibition of neurotransmitter secretion from a target cell or tissue between >3 to ≤13 days after administration; and/or between about 47%-57% (preferably about 52-54%) inhibition of neurotransmitter secretion from the target cell or tissue between >17 to <19 days after administration; and/or between about 45%-55% (preferably about 50%-52%) inhibition of neurotransmitter secretion from the target cell or tissue between >20 to <22 days after administration; and/or between about 25%-35% (preferably about 29%-31%) inhibition of neurotransmitter secretion from the target cell or tissue between >23 to <26 days after administration; and/or between about 25%-35% (preferably about 31%-33%) inhibition of neurotransmitter secretion from the target cell or tissue between >27 to <29 days after administration; and/or between about 25%-35% (preferably about 30%-33%) inhibition of neurotransmitter secretion from the target cell or tissue between >34 to <36 days after administration; and/or between about 1%-10% (preferably about 4%-6%) inhibition of neurotransmitter secretion from the target cell or tissue between >41 to <43 days after administration; and/or ≤15% inhibition of neurotransmitter secretion from the target cell or tissue at >48 days after administration.

In some embodiments it is preferable that the total dose of BoNT/E administered is <0.2 ng, such as 0.04-0.15 ng (or 0.01-0.04 ng). Advantageously, the inventors have found that administering lower doses of BoNT/E (<0.2 ng) achieves at least 40% inhibition of neurotransmitter secretion from a target cell or tissue. Such lower doses are associated with good maximal inhibition of neurotransmitter secretion (e.g. of at least 40% or 50% inhibition), much shorter duration of effect and/or associated with a similar time to maximal effect. This latter point is surprising and in direct contrast with BoNTs comprising complex proteins (e.g. BoNT/A comprising complex proteins), in which the time to achieve the maximal inhibition is much shorter when a higher dose is administered (e.g. a dose of 0.2 ng). For example, the inventors have found that as low as 0.04 ng (40 pg) of BoNT-E (e.g. recombinant BoNT-E) provides the same amplitude of effect (over days 1-7 after administration) as does 20 U BoNT-A (Dysport®)—see Example 4. Notably, 20 U Dysport=108 pg neurotoxin (5.35-5.38 pg neurotoxin/U, typically 5.35 pg neurotoxin/U). This was particularly surprising to the inventors.

In one embodiment BoNT/E is administered at a dose 0.04-0.15 ng (e.g. 0.04 ng) that provides:

at least 40% inhibition of neurotransmitter secretion from a target cell or tissue between >3 to ≤13 days after administration; and/or between about 30%-40% (preferably about 33-35%) inhibition of neurotransmitter secretion from the target cell or tissue between >17 to <19 days after administration; and/or between about 7%-17% (preferably about 12%-14%) inhibition of neurotransmitter secretion from the target cell or tissue between >20 to <22 days after administration; and/or between about 15%-25% (preferably about 21%-23%) inhibition of neurotransmitter secretion from the target cell or tissue between >23 to <26 days after administration; and/or ≤15% inhibition of neurotransmitter secretion from the target cell or tissue in >48 days after administration.

In one embodiment the target tissue is a muscle. Examples of such muscle include the occipitofrontalis, nasalis, orbicularis oris, depressor anguli oris, platysma, sternohyoid, serratus anterior, rectus abdominis, external oblique, tensor fasciae latae, brachioradialis, Iliacus, psoas major, pectineus, adductor longus, sartorius, gracilis, vastus lateralis, rectus femoris, vastus medialis, tendon of quadriceps femoris, patella, gastrocnemius, soleus, tibia, fibularis longus, tibialis anterior, patellar ligament, iliotibial tract, hypothenar muscles, thenar muscles, flexor carpi ulnaris, flexor digitorum superficialis, palmaris longus, flexor carpi radials, brachioradialis, pronator teres, brachialis, biceps brachii, triceps brachii, pectoralismajor, deltoid, trapezius, sternocleidomastoid, masseter, orbicularis oculi, temporalis, epicranial aponeurosis, teres major, extensor digitorum, extensor carpiulnaris, anconeus, abductor policis longus, plantaris, calcanel tendon, soleus, adductor magnus, gluteus maximus, gluteus medius, latissimus dorsi, intraspinatus.

In one embodiment, the target tissue is one or more selected from the corrugator supercilii, triceps brachii, biceps brachii, brachialis, and/or brachioradialis, extensor digitorum, or a combination thereof.

In one embodiment, the target tissue is one or more selected from a flexor carpi radialis, a flexor carpi ulnaris, a flexor digitorum profundus, a flexor digitorum superficialis, a flexor pollicis longus, an adductor pollicis, a brachialis, a brachioradialis, a biceps brachii, a pronator teres, a triceps brachii, pectoralis major, a subscapularis, a latissimus dorsi, or a combination thereof (preferably wherein the BoNT/E is for use in treating upper limb spasticity).

In one embodiment, the target tissue is one or more selected from a flexor carpi radialis, a flexor carpi ulnaris, or a combination thereof. In one embodiment, the target tissue is one or more selected from a flexor digitorum profundus, a flexor digitorum superficialis, a flexor pollicis longus, an adductor pollicis, or a combination thereof. In one embodiment, the target tissue is one or more selected from a brachialis, a brachioradialis, a biceps brachii, a pronator teres, or a combination thereof. In one embodiment, the target tissue is one or more selected from triceps brachii, pectoralis major, a subscapularis, a latissimus dorsi, or a combination thereof.

In one embodiment, the target tissue is one or more selected from soleus muscle, a gastrocnemius (e.g. medial head or lateral head), a tibialis posterior, a flexor digitorum longus, a flexor digitorum brevis, a flexor hallucis longus, a flexor hallucis brevis, or a combination thereof (preferably wherein the BoNT/E is for use in treating lower limb spasticity).

In one embodiment, the target tissue is a soleus muscle. In one embodiment, the target tissue is a gastrocnemius (e.g. medial head or lateral head). In one embodiment, the target tissue is a tibialis posterior, a flexor digitorum longus, a flexor digitorum brevis, a flexor hallucis longus, a flexor hallucis brevis, or a combination thereof.

In one embodiment, the target tissue is one or more selected from a corrugator supercilii, a procerus muscle, an orbicularis oculi, a frontalis muscle or a combination thereof (preferably wherein the BoNT/E is for use in treating an upper facial line).

In one embodiment, the target tissue is a corrugator supercilii, and one or more selected from a procerus muscle, an orbicularis oculi, a frontalis muscle, or a combination thereof. In one embodiment, the target tissue is a procerus muscle, and one or more selected from a corrugator supercilii, an orbicularis oculi, a frontalis muscle, or a combination thereof. In one embodiment, the target tissue is an orbicularis oculi, and one or more selected from a corrugator supercilii, a procerus muscle, a frontalis muscle, or a combination thereof. In one embodiment, the target tissue is a frontalis muscle, and one or more selected from a corrugator supercilii, a procerus muscle, an orbicularis oculi, or a combination thereof.

In one embodiment the target cell is a motor neuron or a sensory neuron. Preferably the target cell is a motor neuron.

The target cell (used synonymously herein with the term "nerve") may be an axillary nerve, phrenic nerve, spinal ganglion, spinal cord nerve, a sympathetic ganglia chain, a pudendal nerve, a common palmar digital nerve, an ulnar nerve, a deep branch of the ulnar nerve, a sciatic nerve, a peroneal nerve, a tibial nerve, a saphenous nerve, an interosseous nerve, a superficial peroneal nerve, an intermediate dorsal cutaneous nerve, a medial plantar nerve, a medial dorsal cutaneous nerve, a deep peroneal nerve, a muscular branches of tibial nerve, an intrapatellar branch of saphenous nerve, a common peroneal nerve, a muscular branch of femoral nerve, an anterior cutaneous branches of femoral nerve, a muscular branches of sciatic nerve, a femoral nerve, an iliolinguinal nerve, a filum terminale nerve, a iliohypogastric nerve, an obturator nerve, a radial nerve, a subcostal nerve, an intercostal nerve, a dorsal branch of an intercostal nerve, a medial cutaneous branch of an intercostal nerve, a musculaneous nerve, a deltoid nerve, a vagus nerve, a brachial plexus nerve, a supraclavicular nerve, a facial nerve, an auriculo temporal nerve, or a combination thereof. In a preferred embodiment, the target cell is a peroneal nerve.

The BoNT/E for use in the present invention may be encoded by a nucleotide sequence having at least 70% sequence identity to SEQ ID NO: 1. In one embodiment BoNT/E for use in the present invention may be encoded by a nucleotide sequence having at least 80% or 90% sequence identity to SEQ ID NO: 1. Preferably BoNT/E for use in the present invention may be encoded by a nucleotide sequence having (or consisting of) SEQ ID NO: 1. Preferably BoNT/E for use in the present invention may be encoded by a nucleotide sequence having (or consisting of) a sequence which is codon-optimised for expression in a heterologous expression system (e.g. SEQ ID NO: 1), such as an *E. coli* host cell.

The BoNT/E for use in the present invention may comprise a polypeptide sequence having at least 70% sequence identity to SEQ ID NO: 2 or SEQ ID NO: 3. In one embodiment BoNT/E for use in the present invention may comprise a polypeptide sequence having at least 80% or 90% sequence identity to SEQ ID NO: 2 or SEQ ID NO: 3. Preferably BoNT/E for use in the present invention comprises (or consists of) a polypeptide sequence shown as SEQ ID NO: 2 or SEQ ID NO: 3.

Preferably BoNT/E for use in the present invention may comprise a polypeptide sequence having at least 70% sequence identity to SEQ ID NO: 2. Preferably BoNT/E for use in the present invention may comprise a polypeptide sequence having at least 80% or 90% sequence identity to SEQ ID NO: 2. More preferably BoNT/E for use in the present invention comprises (or consists of) a polypeptide sequence shown as SEQ ID NO: 2.

The BoNT/E for use in the present invention may comprise a polypeptide sequence having at least 70% sequence identity to SEQ ID NO: 2, with the proviso that the polypeptide sequence includes one or more (for example, one or more, two or more, three or more, four or more, five or more, six or more, seven or more, or eight; preferably all eight) of the following amino acids (wherein the amino acid position numbering starts with the N-terminal methionine amino acid residue and ends with the C-terminal amino acid residue of the BoNT/E protein):

glycine at position 177; serine at position 198; alanine at position 340; leucine at position 773; leucine at position 963; glutamine at position 964; alanine at position 967; asparagine at position 1195.

In one embodiment BoNT/E for use in the present invention may comprise a polypeptide sequence having at least 80% or 90% sequence identity to SEQ ID NO: 2, with the proviso that the polypeptide sequence includes one or more (for example, one or more, two or more, three or more, four or more, five or more, six or more, seven or more, or eight; preferably all eight) of the following amino acids (wherein the amino acid position numbering starts with the N-terminal methionine amino acid residue and ends with the C-terminal amino acid residue of the BoNT/E protein):

glycine at position 177; serine at position 198; alanine at position 340; leucine at position 773; leucine at position 963; glutamine at position 964; alanine at position 967; asparagine at position 1195.

Said amino acids may be substitutions (e.g. mutations) relative to a wild-type BoNT/E polypeptide sequence (such as SEQ ID NO.: 3). For example:

the glycine at position 177 may be an arginine to glycine substitution (R177G);

the serine at position 198 may be a C198S substitution;

the alanine at position 340 may be a R340A substitution;

the leucine at position 773 may be a I173L substitution;

the leucine at position 963 may be a F963L substitution;

the glutamine at position 964 may be a E964Q substitution;

the alanine at position 967 may be a R967A substitution; and/or the asparagine at position 1195 may be an insertion (e.g. and insertion between G1194 and N1195 of a wild-type BoNT/E sequence, such as the polypeptide sequence of SEQ ID NO. 3).

In one embodiment, said one or more amino acids comprise (or consist of) glycine at position 177; serine at position 198; alanine at position 340; leucine at position 773; leucine at position 963; glutamine at position 964; alanine at position 967; and asparagine at position 1195.

In one embodiment, said one or more amino acids comprise (or consist of) glycine at position 177; alanine at position 340; leucine at position 773; leucine at position 963; glutamine at position 964; alanine at position 967; and asparagine at position 1195.

In one embodiment, said one or more amino acids comprise (or consist of) glycine at position 177, and one or more (for example, one or more, two or more, three or more, four or more, five or more, six or more, or seven) of: serine at position 198; alanine at position 340; leucine at position 773; leucine at position 963; glutamine at position 964; alanine at position 967; asparagine at position 1195.

In one embodiment, said one or more amino acids comprise (or consist of) serine at position 198, and one or more (for example, one or more, two or more, three or more, four or more, five or more, six or more, or seven) of: glycine at position 177; alanine at position 340; leucine at position 773; leucine at position 963; glutamine at position 964; alanine at position 967; and asparagine at position 1195.

In one embodiment, said one or more amino acids comprise (or consist of) alanine at position 340, and one or more (for example, one or more, two or more, three or more, four or more, five or more, six or more, or seven) of: glycine at position 177; serine at position 198; leucine at position 773; leucine at position 963; glutamine at position 964; alanine at position 967; asparagine at position 1195.

In one embodiment, said one or more amino acids comprise (or consist of) leucine at position 773, and one or more (for example, one or more, two or more, three or more, four or more, five or more, six or more, or seven) of: glycine at position 177; serine at position 198; alanine at position 340; leucine at position 963; glutamine at position 964; alanine at position 967; asparagine at position 1195.

In one embodiment, said one or more amino acids comprise (or consist of) leucine at position 963, and one or more (for example, one or more, two or more, three or more, four or more, five or more, six or more, or seven) of: glycine at position 177; serine at position 198; alanine at position 340; leucine at position 773; glutamine at position 964; alanine at position 967; asparagine at position 1195.

In one embodiment, said one or more amino acids comprise (or consist of) glutamine at position 964, and one or more (for example, one or more, two or more, three or more, four or more, five or more, six or more, or seven) of: glycine at position 177; serine at position 198; alanine at position 340; leucine at position 773; leucine at position 963; alanine at position 967; asparagine at position 1195.

In one embodiment, said one or more amino acids comprise (or consist of) alanine at position 967, and one or more (for example, one or more, two or more, three or more, four or more, five or more, six or more, or seven) of: glycine at position 177; serine at position 198; alanine at position 340; leucine at position 773; leucine at position 963; glutamine at position 964; asparagine at position 1195.

In one embodiment, said one or more amino acids comprise (or consist of) asparagine at position 1195, and one or more (for example, one or more, two or more, three or more, four or more, five or more, six or more, or seven) of: glycine at position 177; serine at position 198; alanine at position 340; leucine at position 773; leucine at position 963; glutamine at position 964; alanine at position 967.

In one embodiment, the presence of said one or more amino acids, as described above, provides a BoNT/E protein having improved solubility as compared to a BoNT/E protein lacking said amino acid(s). Said improved solubility increases the yield of the protein in a heterologous expression system, such as an *E. coli* expression system.

In one embodiment, the presence of said one or more amino acids, as described above, provides a BoNT/E protein having improved potency as compared to a BoNT/E protein lacking said amino acid(s). Said improved potency may preferably be improved in vivo, potency (more preferably improved in vivo potency in a human subject).

In one embodiment BoNT/E is one described in (or encoded by a nucleotide sequence described in) WO 2014/068317 A1, which is incorporated herein by reference.

BoNT/E is formed from two polypeptide chains, the heavy chain (H-chain), which has a molecular mass of approximately 100 kDa, and the light chain (L-chain), which has a molecular mass of approximately 50 kDa. The H-chain comprises a C-terminal targeting component (receptor binding domain or $H_C$ domain) and an N-terminal translocation component ($H_N$ domain). A BoNT/E which comprises both a H-chain ($H_C$ domain and $H_N$ domain) and an L-chain is referred to as a holotoxin.

In one embodiment, BoNT/E for use in the present invention is a holotoxin.

An exemplary L-chain reference sequence includes amino acid residues 1-422 of BoNT/E. However, this reference sequence should be considered a guide, as slight variations may occur according to sub-serotypes. By way of example, US 2007/0166332 (hereby incorporated by reference in its entirety) cites a slightly different BoNT/E L-chain sequence of amino acid residues M1-R422.

Examples of the BoNT/E $H_C$ domain reference sequence includes amino acid residues R846-K1252.

```
The L-chain of BoNT/E for use in the present invention may be as follows
(SEQ ID NO.: 4):
    1 PKINSFNYND PVNDRTILYI KPGGCQEFYK SFNIMKNIWI IPERNVIGTT

51 PQDFHPPTSL KNGDSSYYDP NYLQSDEEKD RFLKIVTKIF NRINNNLSGG

101 ILLEELSKAN PYLGNDNTPD NQFHIGDASA VEIKFSNGSQ DILLPNVIIM

151 GAEPDLFETN SSNISLRNNY MPSNHGFGSI AIVTFSPEYS FRFNDNSMNE

201 FIQDPALTLM HELIHSLHGL YGAKGITTKY TITQKQNPLI TNIRGTNIEE

251 FLTFGGTDLN IITSAQSNDI YTNLLADYKK IASKLSKVQV SNPLLNPYKD

301 VFEAKYGLDK DASGIYSVNI NKFNDIFKKL YSFTEFDLAT KFQVKCRQTY

351 IGQYKYFKLS NLLNDSIYNI SEGYNINNLK VNFRGQNANL NPRIITPITG

401 RGLVKKIIRF CKNIVSVKGI R

The H-chain of BoNT/E for use in the present invention may be as follows
(SEQ ID NO.: 5):
    1 KSICIEINNG ELFFVASENS YNDDNINTPK EIDDTVTSNN NYENDLDQVI

51 LNFNSESAPG LSDEKLNLTI QNDAYIPKYD SNGTSDIEQH DVNELNVFFY

101 LDAQKVPEGE NNVNLTSSID TALLEQPKIY TFFSSEFINN VNKPVQAALF

151 VSWIQQVLVD FTTEANQKST VDKIADISIV VPYIGLALNI GNEAQKGNFK

201 DALELLGAGI LLEFEPELLI PTILVFTIKS FLGSSDNKNK VIKAINNALK

251 ERDEKWKEVY SFIVSNWMTK INTQFNKRKE QMYQALQNQV NAIKTIIESK

301 YNSYTLEEKN ELTNKYDIKQ IENELNQKVS IAMNNIDRFL TESSISYLMK

351 LINEVKINKL REYDENVKTY LLNYIIQHGS ILGESQQELN SMVTDTLNNS

401 IPFKLSSYTD DKILISYFNK FFKRIKSSSV LNMRYKNDKY VDTSGYDSNI

451 NINGDVYKYP TNKNQFIGYN DKLSEVNISQ NDYIIYDNKY KNFSISFWVR

501 IPNYDNKIVN VNNEYTIINC MRDNNSGWKV SLNHNEIIWT LQDNAGINQK

551 LAFNYGNANG ISDYINKWIF VTITNDRLGD SKLYTNGNLI DQKSILNLGN

601 IHVSDNILFK IVNCSYTRYI GIRYFNIFDK ELDETEIQTL YSNEPNTNIL

651 KDFWGNYLLY DKEYYLLNVL KPNNFIDRRK DSTLSINNIR STILLANRLY

701 SGIKVKIQRV NNSSTNDNLV RKNDQVYINF VASKTHLFPL YADTATTNKE

751 KTIKISSSGN RFNQVVVMNS VGNNCTMNFK NNNGNNIGLL GFKADTVVAS

801 TWYYTHMRDH TNSNGCFWNF ISEEHGWQEK
```

The $H_C$ domain of BoNT/E comprises two distinct structural features that are referred to as the $H_{CC}$ and $H_{CN}$ domains. Amino acid residues involved in receptor binding are believed to be primarily located in the $H_{CC}$ domain. An example of the BoNT/E $H_{CN}$ domain reference sequence includes amino acid residues 846-1085.

The above sequence positions may vary slightly according to sub-type, and further examples of suitable (reference) BoNT/E $H_{CN}$ domains includes amino acid residues 848-1085.

BoNT/E may be produced by *C. botulinum* or *C. butyricum*, preferably *C. botulinum*. In one embodiment, the BoNT/E is produced in a non-clostridial cell. Alternatively (preferably) BoNT/E may be produced in a recombinant form (e.g. in *Escherichia coli*). Thus in one embodiment, BoNT/E for use in the invention is produced in a heterologous expression system, such as an *E. coli*. In one embodiment, the *E. coli* cell is *E. coli* BLR (DE3).

Further details on BoNT/E produced in a heterologous expression system (such as an *E. coli*) are described in WO 2014/068317 A1, which is incorporated herein by reference.

The BoNT/E composition of the present invention is, advantageously, substantially free from trypsin protease (used to activate the single-chain polypeptide), thus preventing unwanted non-specific cleavage of BoNT/E protein.

The BoNT/E composition of the present invention is that the protein content of the composition is provided by the actual neurotoxin (BoNT/E). Thus, administration of say 4 ng of a BoNT/E composition corresponds to an administration of 4 ng of BoNT/E neurotoxin.

In one embodiment, wherein the BoNT/E composition (as described above) is substantially free from trypsin, the composition contains less than 100 picograms (pg) trypsin per 100 nanograms (ng) of BoNT/E protein; for example, less than 50, 20, 10, 9, 8, 7, 6 or 5 pg trypsin per 100 ng of BoNT/E protein. In one embodiment, the composition (as described above) contains less than 10 pg trypsin per 100 ng of BoNT/E protein, or less than 7 pg trypsin per 100 ng of BoNT/E protein, or less than 5 pg trypsin per 100 ng of BoNT/E protein. In a preferred embodiment, the composition (as described above) contains less than 10 pg trypsin per 100 ng of BoNT/E protein, or less than 7 pg trypsin per 100 ng of BoNT/E protein.

Thus, in one embodiment, the phrase "substantially free from trypsin" means less than 100 pg trypsin per 100 ng of BoNT/E protein; for example, less than 50, 20, 10, 9, 8, 7, 6 or 5 pg trypsin per 100 ng of BoNT/E protein, preferably less than 10 pg trypsin per 100 ng of BoNT/E protein, or less than 7 pg trypsin per 100 ng of BoNT/E protein.

Methods for determining the concentration of trypsin in a composition are known in the art (e.g. are described in WO 2014/068317). By way of example, the concentration of trypsin in a composition of the invention may be determined using a sandwich ELISA (Enzyme-Linked Immunosorbent Assay).

BoNT/E is known to cleave the synaptosomal-associated protein of 25 kDa (SNAP-25).

In some embodiments BoNT/E may be a modified BoNT/E or derivative thereof, including but not limited to those described below. A modified BoNT/E or derivative may contain one or more amino acids that has been modified as compared to the native (unmodified) form of BoNT/E, or may contain one or more inserted amino acids that are not present in the native (unmodified) form of BoNT/E. By way of example, a modified BoNT/E may have modified amino acid sequences in one or more domains relative to the native (unmodified) BoNT/E sequence. Such modifications may modify functional aspects of BoNT/E, for example biological activity or persistence. Thus, in one embodiment, BoNT/E is a modified BoNT/E, or a BoNT/E derivative.

A modified BoNT/E may have one or more modifications in the amino acid sequence of the heavy chain (such as a modified $H_C$ domain), wherein said modified heavy chain binds to target nerve cells with a higher or lower affinity than the native (unmodified) BoNT/E. Such modifications in the $H_C$ domain can include modifying residues in the ganglioside binding site of the $H_C$ domain or in the protein (SV2 or synaptotagmin) binding site that alter binding to the ganglioside receptor and/or the protein receptor of the target nerve cell. Examples of such modified clostridial neurotoxins are described in WO 2006/027207 and WO 2006/114308, both of which are hereby incorporated by reference in their entirety.

A modified BoNT/E may have one or more modifications in the amino acid sequence of the light chain, for example modifications in the substrate binding or catalytic domain which may alter or modify the SNARE protein specificity of the modified L-chain. Examples of such modified clostridial neurotoxins are described in WO 2010/120766 and US 2011/0318385, both of which are hereby incorporated by reference in their entirety.

A modified BoNT/E may comprise one or more modifications that increases or decreases the biological activity and/or the biological persistence of the modified BoNT/E. For example, a modified BoNT/E may comprise a leucine- or tyrosine-based motif, wherein said motif increases or decreases the biological activity and/or the biological persistence of the modified BoNT/E. Suitable leucine-based motifs include xDxxxLL, xExxxLL, xExxxIL, and xExxxLM (wherein x is any amino acid). Suitable tyrosine-based motifs include Y-x-x-Hy (wherein Hy is a hydrophobic amino acid). Examples of modified clostridial neurotoxins comprising leucine- and tyrosine-based motifs are described in WO 2002/08268, which is hereby incorporated by reference in its entirety.

The term "BoNT/E" is in one embodiment intended to embrace hybrid and chimeric BoNT/E. A hybrid BoNT/E comprises at least a portion of a light chain from one clostridial neurotoxin or subtype thereof, and at least a portion of a heavy chain from another clostridial neurotoxin or clostridial neurotoxin subtype, wherein at least one of the subtypes is a BoNT/E subtype. In one embodiment the hybrid BoNT/E may contain the entire light chain of a light chain from one clostridial neurotoxin subtype and the heavy chain from another clostridial neurotoxin subtype, wherein at least one of the subtypes is a BoNT/E subtype. In another embodiment, a chimeric clostridial neurotoxin may contain a portion (e.g. the binding domain) of the heavy chain of one clostridial neurotoxin subtype, with another portion of the heavy chain being from another clostridial neurotoxin subtype, wherein at least one of the subtypes is a BoNT/E subtype. Similarly or alternatively, the therapeutic element may comprise light chain portions from different BoNT/E subtypes. Such hybrid or chimeric BoNT/E polypeptides are useful, for example, as a means of delivering the therapeutic benefits thereof to patients who are immunologically resistant to a given clostridial neurotoxin subtype, to patients who may have a lower than average concentration of receptors to a given clostridial neurotoxin heavy chain binding domain, or to patients who may have a protease-resistant variant of the membrane or vesicle toxin substrate (e.g., SNAP-25, VAMP and syntaxin). Hybrid and chimeric clostridial neurotoxins are described in U.S. Pat. No. 8,071, 110, which publication is hereby incorporated by reference in its entirety. Thus, in one embodiment, the BoNT/E of the invention is a hybrid BoNT/E, or a chimeric BoNT/E.

The present invention also embraces BoNT/E having a non-native protease cleavage site. In such BoNT/E polypeptides, the native protease cleavage site (also known as the activation site, as described above) is modified or replaced with a protease cleavage site that is not native to BoNT/E (i.e. an exogenous cleavage site). Such a site will require an exogenous protease for cleavage, which allows for improved control over the timing and location of cleavage events. Non-native protease cleavage sites that may be employed in BoNT/E include:

| Enterokinase | (DDDDK↓) |
| Factor Xa | (IEGR↓/IDGR↓) |
| TEV (Tobacco Etch virus) | (ENLYFQ↓G) |
| Thrombin | (LVPR↓GS) |
| PreScission | (LEVLFQ↓GP). |

Additional protease cleavage sites include recognition sequences that are cleaved by a non-cytotoxic protease, for example by the light chain of a clostridial neurotoxin. These include the SNARE (e.g. SNAP-25, syntaxin, VAMP) protein recognition sequences that are cleaved by non-cytotoxic proteases such as the light chain of a clostridial neurotoxin. Clostridial neurotoxins comprising non-native protease cleavage sites are described in U.S. Pat. No. 7,132,259, EP 1206554-B2 and US 2007/0166332, all of which are hereby incorporated by reference in their entirety. Also embraced by the term protease cleavage site is an intein, which is a self-cleaving sequence. The self-splicing reaction is controllable, for example by varying the concentration of reducing agent present.

The present invention also embraces BoNT/E comprising a "destructive cleavage site". In said BoNT/E polypeptides, a non-native protease cleavage site is incorporated into BoNT/E, at a location chosen such that cleavage at said site will decrease the activity of, or inactivate, BoNT/E. The destructive protease cleavage site can be susceptible to cleavage by a local protease, in the event that BoNT/E, following administration, migrates to a non-target location. Suitable non-native protease cleavage sites include those described above. Clostridial neurotoxins comprising a destructive cleavage site are described in WO 2010/094905 and WO 2002/044199, both of which are hereby incorporated by reference in their entirety.

In one embodiment, the BoNT/E comprises a native cleavage site.

In one embodiment, the BoNT/E does not comprise an E3 ligase recognition motif.

BoNT/E, especially the light chain component thereof, may be PEGylated—this may help to increase stability, for example duration of action of the light chain component. PEGylation preferably includes the addition of PEG to the N-terminus of the light chain component. By way of example, the N-terminus of a light chain may be extended with one or more amino acid (e.g. cysteine) residues, which may be the same or different. One or more of said amino acid residues may have its own PEG molecule attached (e.g. covalently attached) thereto. An example of this technology is described in WO2007/104567, which is hereby incorporated by reference in its entirety.

The BoNT/E for use in the present invention can be produced using recombinant nucleic acid technologies.

BoNT/E for use in the present invention may be prepared by a method comprising expressing a nucleic acid encoding BoNT/E in a suitable host cell, lysing the host cell to provide a host cell homogenate containing the single-chain BoNT/E, and isolating the single-chain BoNT/E. Prior to use in the present invention the single-chain BoNT/E is preferably proteolytically processed into a corresponding active di-chain BoNT/E by contacting the single-chain BoNT/E with a protease that hydrolyses a peptide bond in the BoNT/E activation loop thereby producing a di-chain BoNT/E (e.g. wherein the light chain and heavy chain are joined together by a disulphide bond).

Preferably, said host cell provides a heterologous (e.g. non-clostridial) expression system. Preferably, the host cell is *E. coli*.

The BoNT/E for use in the present invention is preferably in a di-chain form.

BoNT/E may be used in the present invention as part of a pharmaceutical composition. The pharmaceutical composition may comprise BoNT/E and a pharmaceutically acceptable carrier, excipient, adjuvant, and/or salt. Thus, in one embodiment BoNT/E may be administered in combination with a pharmaceutically acceptable carrier, excipient, adjuvant, and/or salt.

BoNT/E may be formulated for parenteral, continuous infusion or topical application. In one embodiment, BoNT/E is formulated for parenteral administration, such as by subcutaneous injection, intradermal injection and/or intramuscular injection. Preferably, BoNT/E is formulated for parenteral administration, such as by way of more preferably for intramuscular administration (e.g. by injection).

Compositions suitable for injection may be in the form of solutions, suspensions or emulsions, or dry powders which are dissolved or suspended in a suitable vehicle prior to use.

In the case of BoNT/E that is to be delivered locally, BoNT/E may be formulated as a cream (e.g. for topical application), or for sub-dermal injection.

Local delivery means may include an aerosol, or other spray (e.g. a nebuliser).

Fluid dosage forms are typically prepared utilising BoNT/E and a pyrogen-free sterile vehicle. The BoNT/E, depending on the vehicle and concentration used, can be either dissolved or suspended in the vehicle. In preparing solutions the BoNT/E can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration.

The components may be isolated in a sterile state or alternatively it may be sterilised after isolation, e.g. by gamma irradiation.

Advantageously, a suspending agent for example polyvinylpyrrolidone is included in the composition(s) to facilitate uniform distribution of the components.

Administration in accordance with the present invention may take advantage of a variety of delivery technologies including microparticle encapsulation, viral delivery systems or high-pressure aerosol impingement. BoNT/E may be administered to a patient by intrathecal or epidural injection in the spinal column at the level of the spinal segment involved in the innervation of an affected organ.

The dosage ranges for administration of the BoNT/E are those to produce the desired therapeutic effect (e.g. those described above). The dosages may also be based on CBA units as described in the Examples.

In one embodiment a disorder of the present invention is one or more of: a condition associated with strabismus, blepharospasm, squint, dystonia (e.g. spasmodic dystonia, oromandibular dystonia, focal dystonia, tardive dystonia, laryngeal dystonia, limb dystonia, cervical dystonia), torticollis (e.g. spasmodic torticollis), beauty therapy (cosmetic) applications benefiting from cell/muscle incapacitation (via SNARE down-regulation or inactivation), neuromuscular disorder or condition of ocular motility (e.g. concomitant strabismus, vertical strabismus, lateral rectus palsy, nystagmus, dysthyroid myopathy), writer's cramp, blepharospasm, bruxism, Wilson's disease, tremor, tics, segmental myoclonus, spasms, spasticity due to chronic multiple sclerosis, spasticity resulting in abnormal bladder control, animus, back spasm, charley horse, tension headaches, levator pelvic syndrome, spina bifida, tardive dyskinesia, Parkinson's disease, stuttering, hemifacial spasm, eyelid disorder, cerebral palsy, focal spasticity, spasmodic colitis, neurogenic bladder, animus, limb spasticity (e.g. lower limb spasticity or upper limb spasticity), tics, tremors, bruxism, anal fissure, achalasia, dysphagia, lacrimation, hyperhidrosis, excessive salivation, excessive gastrointestinal secretions, muscle pain (e.g. pain from muscle spasms), headache pain (e.g. tension headache), brow furrows, skin wrinkles (e.g. upper facial lines, such as glabellar lines, lateral canthal lines and/or frontalis lines), cancer, uterine disorders, uro-genital disorders, urogenital-neurological disorders, chronic neurogenic inflammation, and a smooth muscle disorder.

In one embodiment the disorder is lower limb spasticity. Preferably, the lower limb spasticity is in a subject over the age of 18 years.

In one embodiment the disorder is upper limb spasticity. Preferably, the upper limb spasticity is in a subject over the age of 18 years.

The present invention also encompasses cosmetic methods comprising the use of BoNT/E. For example, the cosmetic method may be for treating upper facial lines (such as glabellar lines, lateral canthal lines and frontalis lines).

In one embodiment, the cosmetic method is for treating glabellar lines, and one or more selected from lateral canthal lines and frontalis lines. In one embodiment, the cosmetic method is for treating lateral canthal lines, and one or more selected from glabellar lines and frontalis lines. In one embodiment, the cosmetic method is for treating frontalis lines, and one or more selected from glabellar lines and lateral canthal lines.

A cosmetic method of the invention may comprise administering (an effective amount) of BoNT/E to treat glabellar lines, lateral canthal lines and/or frontalis lines, wherein the BoNT/E is administered at a site to treat said glabellar lines, lateral canthal lines and/or frontalis lines either simultaneously, or sequentially, such that each of said glabellar lines, lateral canthal lines and/or frontalis lines are treated (preferably concomitantly treated).

Preferably, the cosmetic method is for treating glabellar lines. The glabellar lines may be moderate or severe (e.g. as determined by a physician).

Embodiments related to the use of BoNT/E are intended to be applied equally to the methods of treatment and cosmetic methods described herein and vice versa.

In one embodiment, the human subject is male.

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

ALIGNMENT SCORES FOR DETERMINING SEQUENCE IDENTITY

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of indentical matched}}{[\text{length of the longer sequence plus the number of gaps introduced into the longer sequence in order to align the two sequences}]} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

Basic: arginine
   lysine
   histidine
Acidic: glutamic acid
   aspartic acid
Polar: glutamine
   asparagine
Hydrophobic: leucine
   isoleucine
   valine
Aromatic: phenylalanine
   tryptophan
   tyrosine
Small: glycine
   alanine
   serine
   threonine
   methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylgly-cine, allo-threonine, methyl-threonine, hydroxy-ethylcyste-ine, hydroxyethyl homo-cysteine, nitro-glutamine, homoglutamine, pipecolic acid, tert-leucine, norvaline, 2-azaphenylalanine, 3-azaphenyl-alanine, 4-azaphenyl-ala-nine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and amino-acylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically amino-acylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-aza-phenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be con-verted to non-naturally occurring species by in vitro chemi-cal modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation;

amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a botulinum neurotoxin" includes a plurality of such candidate agents and reference to "the botulinum neurotoxin" includes reference to one or more botulinum neurotoxins and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

Figure 1A:
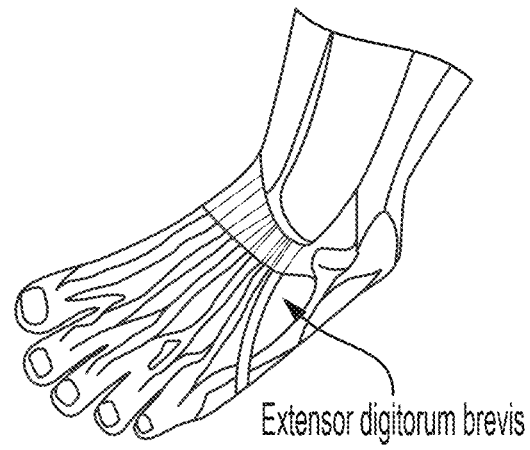
FIG. 1 shows (A) the location of the extensor digitorum brevis muscle, and (B) a representation of the recorded action potential.

SEQUENCE LISTING
Where an initial Met amino acid residue or a corresponding initial codon is indicated in any of the following SEQ ID NOs, said residue/codon may be optional.

(Nucleotide Sequence of BoNT/E)

SEQ ID NO: 1

```
  1 atgccaaaaa ttaatagttt taattataat gatcctgtta atgatagaac aattttatat 61 attaaaccag gcggttgtca agaattttat aaatcattta atattatgaa aaatatttgg 121 ataattccag agagaaatgt aattggtaca acccccaag attttcatcc gcctacttca 181 ttaaaaaatg gagatagtag ttattatgac cctaattatt tacaaagtga tgaagaaaag 241 gatagatttt taaaaatagt cacaaaaata tttaataaaa taaataataa tctttcagga 301 gggatttat tagaagaact gtcaaaagct aatccatatt tagggaatga taatactcca 361 gataatcaat tccatattgg tgatgcatca gcagttgaga ttaaattctc aaatggtagc 421 caagacatac tattacctaa tgttattata atgggagcag agcctgattt atttgaaact 481 aacagttcca atatttctct aagaaataat tatatgccaa gcaatcacgg ttttggatca 541 atagctatag taacattctc acctgaatat tcttttagat ttaatgataa tagtatgaat 601 gaatttattc aagatcctgc tcttacatta atgcatgaat taatacattc attacatgga 661 ctatatgggg ctaaagggat tactacaaag tatactataa cacaaaaaca aaatcccta 721 ataacaaata taagaggtac aaatattgaa gaattcttaa cttttggagg tactgattta 781 aacattatta ctagtgctca gtccaatgat atctatacta atcttctagc tgattataaa
```

-continued

```
 841 aaaatagcgt ctaaacttag caaagtacaa gtatctaatc cactacttaa tccttataaa 901 gatgtttttg aagcaaagta tggattagat aaagatgcta gcggaattta ttcggtaaat 961 ataaacaaat ttaatgatat ttttaaaaaa ttatacagct ttacggaatt tgatttagca 1021 actaaatttc aagttaaatg taggcaaact tatattggac agtataaaata cttcaaactt 1081 tcaaacttgt taaatgattc tatttataat atatcagaag gctataatat aaataattta 1141 aaggtaaatt ttagaggaca gaatgcaaat ttaaatccta gaattattac accaattaca 1201 ggtagaggac tagtaaaaaa aatcattaga ttttgtaaaa atattgtttc tgtaaaaggc 1261 ataaggaaat caatatgtat cgaaataaat aatggtgagt tattttttgt ggcttccgag 1321 aatagttata atgatgataa tataaatact cctaaagaaa ttgacgatac agtaacttca 1381 aataataatt atgaaaatga tttagatcag gttattttaa attttaatag tgaatcagca 1441 cctggacttt cagatgaaaa attaaattta actatccaaa atgatgctta tataccaaaa 1501 tatgattcta atggaacaag tgatatagaa caacatgatg ttaatgaact taatgtattt 1561 ttctatttag atgcacagaa agtgcccgaa ggtgaaaata atgtcaatct cacctcttca 1621 attgatacag cattattaga acaacctaaa atatatacat tttttcatc agaatttatt 1681 aataatgtca ataaacctgt gcaagcagca ttatttgtaa gctggataca acaagtgtta 1741 gtagatttta ctactgaagc taaccaaaaa agtactgttg ataaaattgc agatatttct 1801 atagttgttc catatatagg tcttgcttta aatataggaa atgaagcaca aaaaggaaat 1861 tttaaagatg cacttgaatt attaggagca ggtattttat tagaatttga acccgagctt 1921 ttaattccta caattttagt attcacgata aaatctttt taggttcatc tgataataaa 1981 aataaagtta ttaaagcaat aaataatgca ttgaaagaaa gagatgaaaa atggaaagaa 2041 gtatatagtt ttatagtatc gaattggatg actaaaatta atacacaatt taataaaaga 2101 aaagaacaaa tgtatcaagc tttacaaaat caagtaaatg caattaaaac aataatagaa 2161 tctaagtata atagttatac tttagaggaa aaaaatgagc ttacaaataa atatgatatt 2221 aagcaaatag aaaatgaact taatcaaaag gtttctatag caatgaataa tatagacagg 2281 ttcttaactg aaagttctat atcctattta atgaaattaa taaatgaagt aaaaattaat 2341 aaattaagag aatatgatga gaatgtcaaa acgtatttat tgaattatat tatacaacat 2401 ggatcaatct tgggagagag tcagcaagaa ctaaattcta tggtaactga taccctaaat 2461 aatagtattc cttttaagct ttcttcttat acagatgata aaattttaat ttcatatttt 2521 aataaaattct ttaagagaat taaaagtagt tcagttttaa atatgagata taaaaatgat 2581 aaatacgtag atacttcagg atatgattca aatataaaata ttaatggaga tgtatataaa 2641 tatccaacta ataaaaatca atttggaata tataatgata aacttagtga agttaatata 2701 tctcaaaatg attacattat atatgataat aaatataaaa attttagtat tagtttttgg 2761 gtaagaattc ctaactatga taataagata gtaaatgtta ataatgaata cactataata 2821 aattgtatga gagataataa ttcaggatgg aaagtatctc ttaatcataa tgaaataatt 2881 tggacattgc aagataatgc aggaattaat caaaaattag catttaacta tggtaacgca 2941 aatggtattt ctgattatat aaataagtgg attttgtaa ctataactaa tgatagatta 3001 ggagattcta aactttatat taatggaaat ttaatagatc aaaaatcaat tttaaattta 3061 ggtaatattc atgttagtga caatatatta tttaaaatag ttaattgtag ttatacaaga 3121 tatattggta ttagatattt taatatttt gataaagaat tagatgaaac agaaattcaa 3181 actttatata gcaatgaacc taatacaaat attttgaagg attttggggg aaattatttg 3241 ctttatgaca agaatactaa tttattaaat gtgttaaaac caaataactt tattgatagg
```

-continued

```
3301 agaaaagatt ctactttaag cattaataat ataagaagca ctattctttt agctaataga 3361 ttatatagtg gaataaaagt taaaatacaa agagttaata atagtagtac taacgataat 3421 cttgttagaa agaatgatca ggtatatatt aattttgtag ccagcaaaac tcacttattt 3481 ccattatatg ctgatacagc taccacaaat aaagagaaaa caataaaaat atcatcatct 3541 ggcaatagat ttaatcaagt agtagttatg aattcagtag gaaataattg tacaatgaat 3601 tttaaaaata ataatggaaa taatattggg ttgttaggtt tcaaggcaga tactgtagtt 3661 gctagtactt ggtattatac acatatgaga gatcatacaa acagcaatgg atgtttttgg 3721 aactttattt ctgaagaaca tggatggcaa gaaaaataa
```

(Polypeptide Sequence of BoNT/E)

SEQ ID NO: 2

```
PKINSFNYNDPVNDRTILYIKPGGCQEFYKSFNIMKNIWIIPE

RNVIGTTPQDFHPPTSLKNGDSSYYDPNYLQSDEEKDRFLKIVTKIFNRINNNLSGGI

LLEELSKANPYLGNDNTPDNQFHIGDASAVEIKFSNGSQDILLPNVIIMGAEPDLFET

NSSNISLRNNYMPSNHGFGSIAIVTFSPEYSFRFNDNSMNEFIQDPALTLMHELIHSL

HGLYGAKGITTKYTITQKQNPLITNIRGTNIEEFLTFGGTDLNIITSAQSNDIYTNLL

ADYKKIASKLSKVQVSNPLLNPYKDVFEAKYGLDKDASGIYSVNINKFNDIFKKLYSF

TEFDLATKFQVKCRQTYIGQYKYFKLSNLLNDSIYNISEGYNINNLKVNFRGQNANLN

PRIITPITGRGLVKKIIRFCKNIVSVKGIRKSICIEINNGELFFVASENSYNDDNINT

PKEIDDTVTSNNNYENDLDQVILNFNSESAPGLSDEKLNLTIQNDAYIPKYDSNGTSD

IEQHDVNELNVFFYLDAQKVPEGENNVNLTSSIDTALLEQPKIYTFFSSEFINNVNKP

VQAALFVSWIQQVLVDFTTEANQKSTVDKIADISIVVPYIGLALNIGNEAQKGNFKDA

LELLGAGILLEFEPELLIPTILVFTIKSFLGSSDNKNKVIKAINNALKERDEKWKEVY

SFIVSNWMTKINTQFNKRKEQMYQALQNQVNAIKTIIESKYNSYTLEEKNELTNKYDI

KQIENELNQKVSIAMNNIDRFLTESSISYLMKLINEVKINKLREYDENVKTYLLNYII

QHGSILGESQQELNSMVTDTLNNSIPFKLSSYTDDKILISYFNKFFKRIKSSSVLNMR

YKNDKYVDTSGYDSNININGDVYKYPTNKNQFGIYNDKLSEVNISQNDYIIYDNKYKN

FSISFWVRIPNYDNKIVNVNNEYTIINCMRDNNSGWKVSLNHNEIIWTLQDNAGINQK

LAFNYGNANGISDYINKWIFVTITNDRLGDSKLYINGNLIDQKSILNLGNIHVSDNIL

FKIVNCSYTRYIGIRYFNIFDKELDETEIQTLYSNEPNTNILKDFWGNYLLYDKEYYL

LNVLKPNNFIDRRKDSTLSINNIRSTILLANRLYSGIKVKIQRVNNSSTNDNLVRKND

QVYINFVASKTHLFPLYADTATTNKEKTIKISSSGNRFNQVVVMNSVGNNCTMNFKNN

NGNNIGLLGFKADTVVASTWYYTHMRDHTNSNGCFWNFISEEHGWQEK
```

(BoNT/E-UniProt Q00496)

SEQ ID NO: 3

```
MPKINSFNYNDPVNDRTILYIKPGGCQEFYKSFNIMKNIWIIPERNVIGTTPQDFHPPTS

LKNGDSSYYDPNYLQSDEEKDRFLKIVTKIFNRINNNLSGGILLEELSKANPYLGNDNTP

DNQFHIGDASAVEIKFSNGSQDILLPNVIIMGAEPDLFETNSSNISLRNNYMPSNHRFGS

IAIVTFSPEYSFRFNDNCMNEFIQDPALTLMHELIHSLHGLYGAKGITTKYTITQKQNPL

ITNIRGTNIEEFLTFGGTDLNIITSAQSNDIYTNLLADYKKIASKLSKVQVSNPLLNPYK

DVFEAKYGLDKDASGIYSVNINKFNDIFKKLYSFTEFDLRTKFQVKCRQTYIGQYKYFKL

SNLLNDSIYNISEGYNINNLKVNFRGQNANLNPRIITPITGRGLVKKIIRFCKNIVSVKG

IRKSICIEINNGELFFVASENSYNDDNINTPKEIDDTVTSNNNYENDLDQVILNFNSESA
```

-continued

PGLSDEKLNLTIQNDAYIPKYDSNGTSDIEQHDVNELNVFFYLDAQKVPEGENNVNLTSS

IDTALLEQPKIYTFFSSEFINNVNKPVQAALFVSWIQQVLVDFTTEANQKSTVDKIADIS

IVVPYIGLALNIGNEAQKGNFKDALELLGAGILLEFEPELLIPTILVFTIKSFLGSSDNK

NKVIKAINNALKERDEKWKEVYSFIVSNWMTKINTQFNKRKEQMYQALQNQVNAIKTIIE

SKYNSYTLEEKNELTNKYDIKQIENELNQKVSIAMNNIDRFLTESSISYLMKIINEVKIN

KLREYDENVKTYLLNYIIQHGSILGESQQELNSMVTDTLNNSIPFKLSSYTDDKILISYF

NKFFKRIKSSSVLNMRYKNDKYVDTSGYDSNININGDVYKYPTNKNQFGIYNDKLSEVNI

SQNDYIIYDNKYKNFSISFWVRIPNYDNKIVNVNNEYTIINCMRDNNSGWKVSLNHNEII

WTFEDNRGINQKLAFNYGNANGISDYINKWIFVTITNDRLGDSKLYINGNLIDQKSILNL

GNIHVSDNILFKIVNCSYTRYIGIRYFNIFDKELDETEIQTLYSNEPNTNILKDFWGNYL

LYDKEYYLLNVLKPNNFIDRRKDSTLSINNIRSTILLANRLYSGIKVKIQRVNNSSTNDN

LVRKNDQVYINFVASKTHLFPLYADTATTNKEKTIKISSSGNRFNQVVVMNSVGNCTMNF

KNNNGNNIGLLGFKADTVVASTWYYTHMRDHTNSNGCFWNFISEEHGWQEK (Polypeptide Sequence of BoNT/E L-Chain)

SEQ ID NO: 4

PKINSFNYNDPVNDRTILYIKPGGCQEFYKSFNIMKNIWIIPE

RNVIGTTPQDFHPPTSLKNGDSSYYDPNYLQSDEEKDRFLKIVTKIFNRINNNLSGGI

LLEELSKANPYLGNDNTPDNQFHIGDASAVEIKFSNGSQDILLPNVIIMGAEPDLFET

NSSNISLRNNYMPSNHGFGSIAIVTFSPEYSFRFNDNSMNEFIQDPALTLMHELIHSL

HGLYGAKGITTKYTITQKQNPLITNIRGTNIEEFLTFGGTDLNIITSAQSNDIYTNLL

ADYKKIASKLSKVQVSNPLLNPYKDVFEAKYGLDKDASGIYSVNINKFNDIFKKLYSF

TEFDLATKFQVKCRQTYIGQYKYFKLSNLLNDSIYNISEGYNINNLKVNFRGQNANLN

PRIITPITGRGLVKKIIRFCKNIVSVKGIR (Polypeptide Sequence of BoNT/E H-Chain)

SEQ ID NO: 5

KSICIEINNGELFFVASENSYNDDNINT

PKEIDDTVTSNNNYENDLDQVILNFNSESAPGLSDEKLNLTIQNDAYIPKYDSNGTSD

IEQHDVNELNVFFYLDAQKVPEGENNVNLTSSIDTALLEQPKIYTFFSSEFINNVNKP

VQAALFVSWIQQVLVDFTTEANQKSTVDKIADISIVVPYIGLALNIGNEAQKGNFKDA

LELLGAGILLEFEPELLIPTILVFTIKSFLGSSDNKNKVIKAINNALKERDEKWKEVY

SFIVSNWMTKINTQFNKRKEQMYQALQNQVNAIKTIIESKYNSYTLEEKNELTNKYDI

KQIENELNQKVSIAMNNIDRFLTESSISYLMKLINEVKINKLREYDENVKTYLLNYII

QHGSILGESQQELNSMVTDTLNNSIPFKLSSYTDDKILISYFNKFFKRIKSSSVLNMR

YKNDKYVDTSGYDSNININGDVYKYPTNKNQFGIYNDKLSEVNISQNDYIIYDNKYKN

FSISFWVRIPNYDNKIVNVNNEYTIINCMRDNNSGWKVSLNHNEIIWTLQDNAGINQK

LAFNYGNANGISDYINKWIFVTITNDRLGDSKLYINGNLIDQKSILNLGNIHVSDNIL

FKIVNCSYTRYIGIRYFNIFDKELDETEIQTLYSNEPNTNILKDFWGNYLLYDKEYYL

LNVLKPNNFIDRRKDSTLSINNIRSTILLANRLYSGIKVKIQRVNNSSTNDNLVRKND

QVYINFVASKTHLFPLYADTATTNKEKTIKISSSGNRFNQVVVMNSVGNNCTMNFKNN

NGNNIGLLGFKADTVVASTWYYTHMRDHTNSNGCFWNFISEEHGWQEK

EXAMPLES

Materials & Methods

Pharmacodynamic Model

The pharmacodynamic model utilised the Extensor Digitorum Brevis (EDB) muscle (FIG. 1A). The EDB is a superficial muscle of the foot, accessible for electrophysiological studies. It is involved in the extension of the 2nd to 4th digits of the foot, and weakness thereof does not impair walking.

The EDB muscle was previously used to determine the effect of BoNT/A as published in Hamjian and Walker (1994), Muscle Nerve, 17(12): 1385-92. Since then, the model has been widely used for:

Quantifying onset and degree of human muscle relaxation and duration of effects following BoNT injection (Sloop et al (1996), Neurology, 46(5), 1382-6);

Comparing different subtypes of BoNT (e.g. BoNT/B vs. BoNT/A) (Sloop et al (1997), Neurology, 49(1), 189-94);

Checking potency of BoNT/A formulations (Park and Ahn (2013), J Clin Neurol, 9(3), 157-164).

Figure 1B:
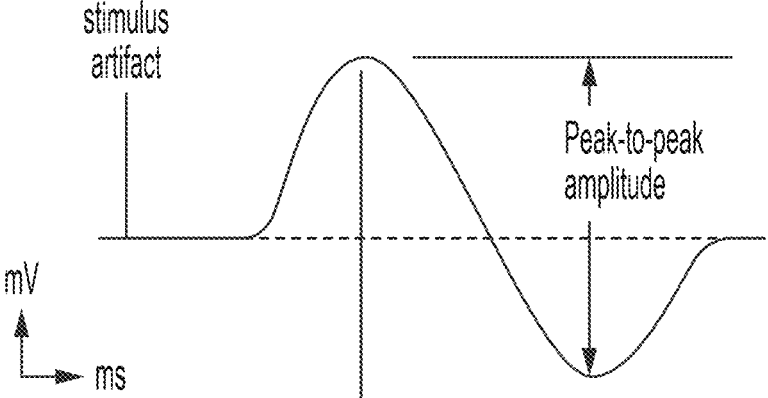

The method involved the stimulation of the injected EDB and recording of its action potential (FIG. 1B). BoNT/E or BoNT/A was administered by way of ultrasound-guided administration and surface electrodes were used for stimulation and recording of action potentials.

Figure 2:
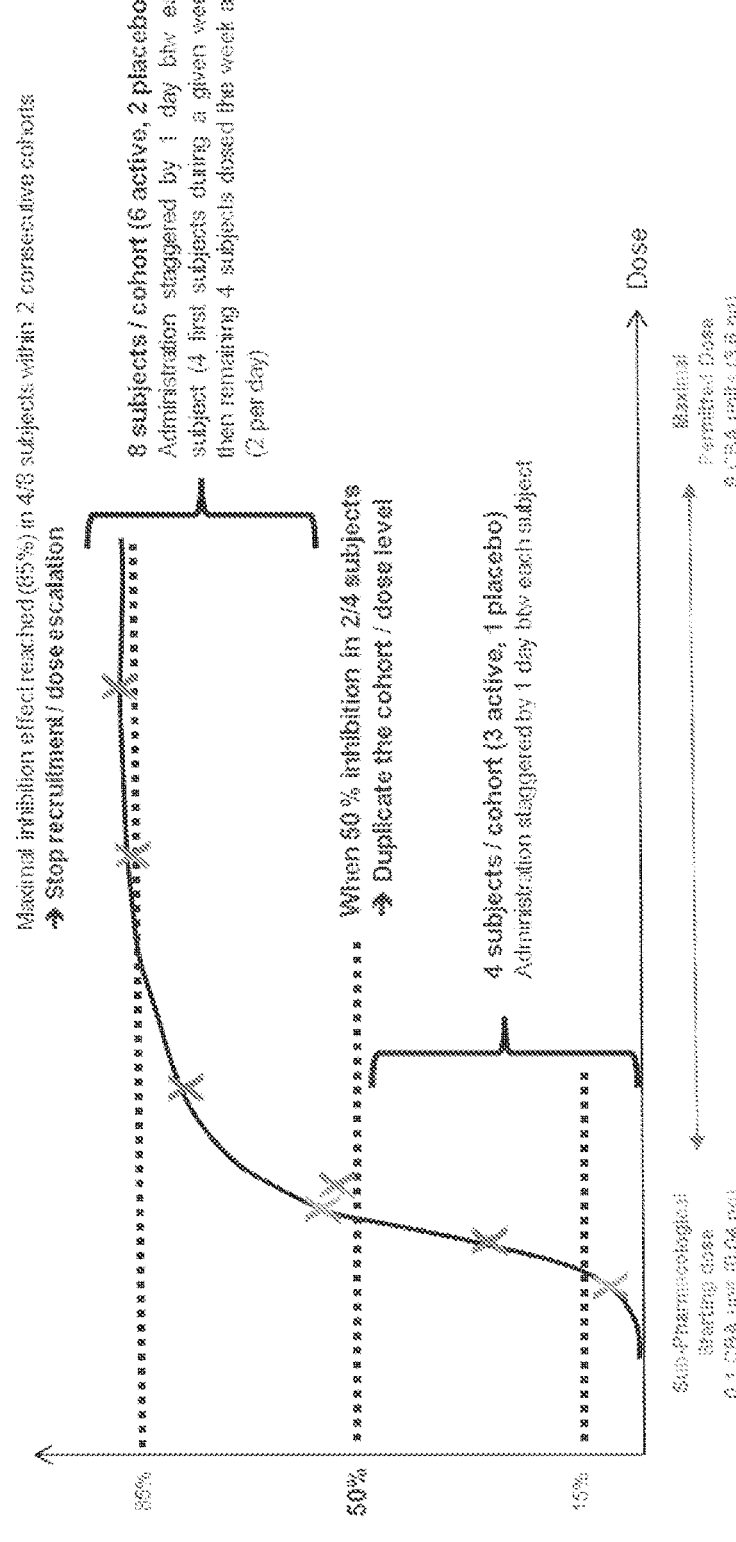
FIG. 2 shows the BoNT/E dose escalation procedure and results.

FIG. 2 summarises the dose escalation procedure, which was based on review of safety (blinded) and pharmacodynamic (anonymized) data from a previous cohort.

Study Design and Treatment

Phase 1, randomised, double-blind, placebo-controlled study (human clinical trial) was conducted.

Each subject received a single intramuscular dose of rBoNT-E or placebo (randomised 3:1) into their right EDB muscle.

Cohorts of subjects were used, with each cohort injected with a higher dose of rBoNT-E than the previous. All subjects in each cohort received the same dose of rBoNT-E, or a placebo.

There was a maximum of eight cohorts:

Initial cohorts: four subjects per cohort (three rBoNT-E, one placebo).

Later cohorts: Once ~50% inhibition of CMAP from baseline was achieved at three consecutive timepoints in at least of three rBoNT-E-injected subjects, cohorts were doubled to eight subjects.

Cohorts were injected sequentially in order of ascending doses:

Doses were escalated until maximal CMAP inhibition (85% reduction from baseline) was achieved at three consecutive timepoints in at least four of six rBoNT-E-injected subjects per cohort, in two consecutive cohorts.

Doses used were: 0.1 cell-based assay units (CBA U; 0.04 ng), 0.5 CBA U (0.2 ng), 2.25 CBA U (0.9 ng) and 9.0 CBA U (3.6 ng).

Inclusion criteria included:

Healthy male adults (18 to 55 years), with body mass index 18 to 30 kg/m$^2$.

EDB CMAP total amplitude of mV by stimulating peroneal nerve for electrophysiological examination (at screening and prior to injection).

Willing to comply with the study protocol and remain at the clinic for the required duration.

Exclusion criteria included:

Previous BoNT treatment months prior to enrolment.

History of hypersensitivity to components of rBoNT-E formulation.

Medical conditions that put the subject at risk with BoNT exposure.

Use of neuromuscular transmission agents.

Cell-Based Assay

The biological activity of rBoNT/E was determined with a cell-based assay (CBA) and is expressed in % relative potency to a defined reference standard. This CBA mimics the in vivo mechanism of action of BoNT/E, i.e. binding to receptors leading to internalisation of the toxin and cleavage of the synaptosomal-associated protein 25 (SNAP25) by the light chain endopeptidase domain. The CBA uses Neuro-2A, a murine neuroblastoma cell line, engineered to express a reporter which utilises a full-length SNAP-25 flanked by fluorophores, cyan fluorescent protein and yellow fluorescent protein (YFP). When the engineered cells are incubated with BoNT/E the toxin binds, and is internalised via receptor-mediated endocytosis, leading to release of the BoNT/E light chain into the cytosol. The endopeptidase light chain cleaves SNAP-25 in the reporter resulting in the release of a C-terminal reporter fragment into the cytosol that contains residues of SNAP-25 and YFP. The fragment is rapidly degraded, resulting in a loss of YFP fluorescence. Recombinant BoNT/E bioactivity is only detected if the toxin enters the cells through the BoNT/E H-chain receptor binding, internalisation, and translocation activities; thus, the in vitro CBA mimics the natural cell biology of BoNT/E. The CBA units corresponding to the amounts of BoNT/E are provided in the following Examples.

1 CBA unit may be defined as the amount of BoNT/E required to cleave 1 nM of substrate (SNAP-25) in 1 minute.

Example 1

Administration of BoNT/E

Figure 3:
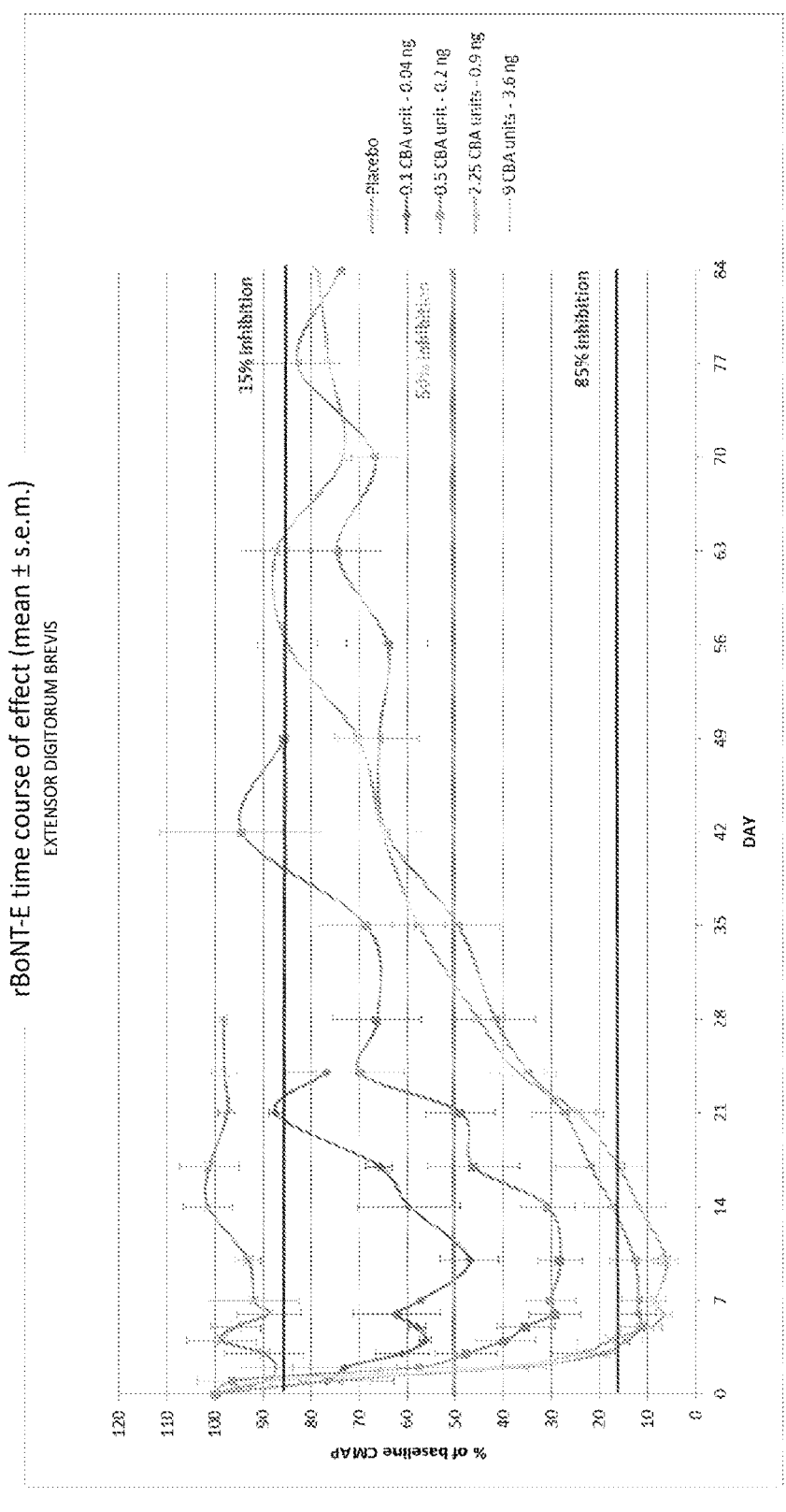
FIG. 3 shows the % of baseline compound muscle action potential (CMAP) of the stimulated extensor digitorum brevis muscle over a 12 week period following administration of different doses of rBoNT/E compared to placebo (mean+/−s.e.m.).

FIG. 3 shows that the placebo varies around the 100% CMAP baseline, and shows a clear dose-effect for BoNT/E. The two higher doses showed the same pharmacodynamic (PD) profile with maximal inhibition (more than 90%) reached, and a duration of action of approximately 50 days (15% inhibition cut-off) or 30 days (50% inhibition cut-off).

Administration of Dysport®

FIG. 4 again shows the placebo varying around 100% baseline, and a 60-70% inhibition reached for the doses of 40 and 70 U of Dysport® (BoNT/A). The inhibition plateaued for several weeks with no recovery (return to 15% inhibition) at the end of the 26-week follow-up period.

Example 2

Analysis up to 26 Weeks Post-Administration

Figure 4:
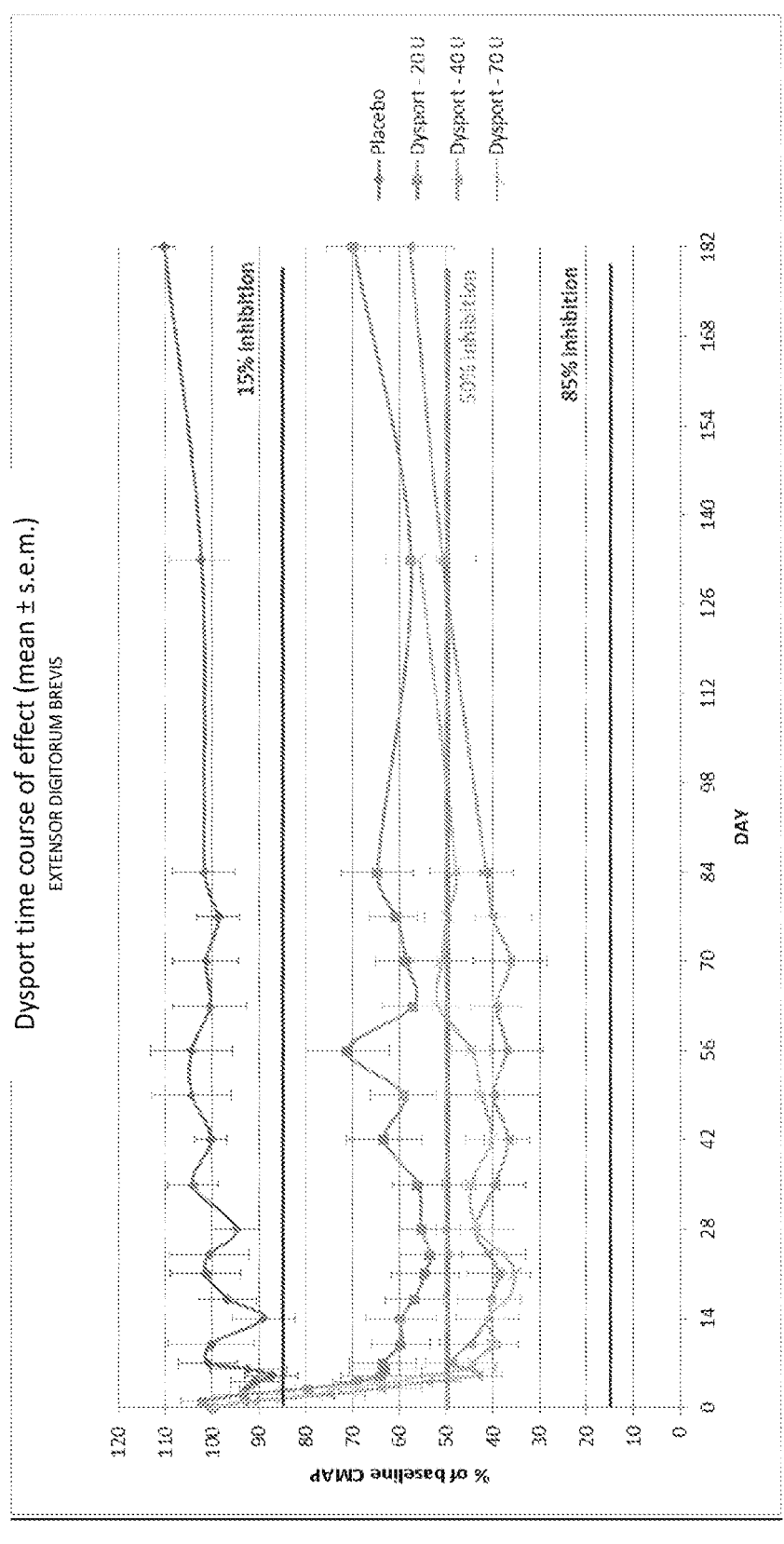
FIG. 4 shows the % of baseline compound muscle action potential (CMAP) of the stimulated extensor digitorum brevis muscle over a 26 week period following administration of different doses of Dysport® compared to placebo (mean+/−s.e.m.).
Figure 5:
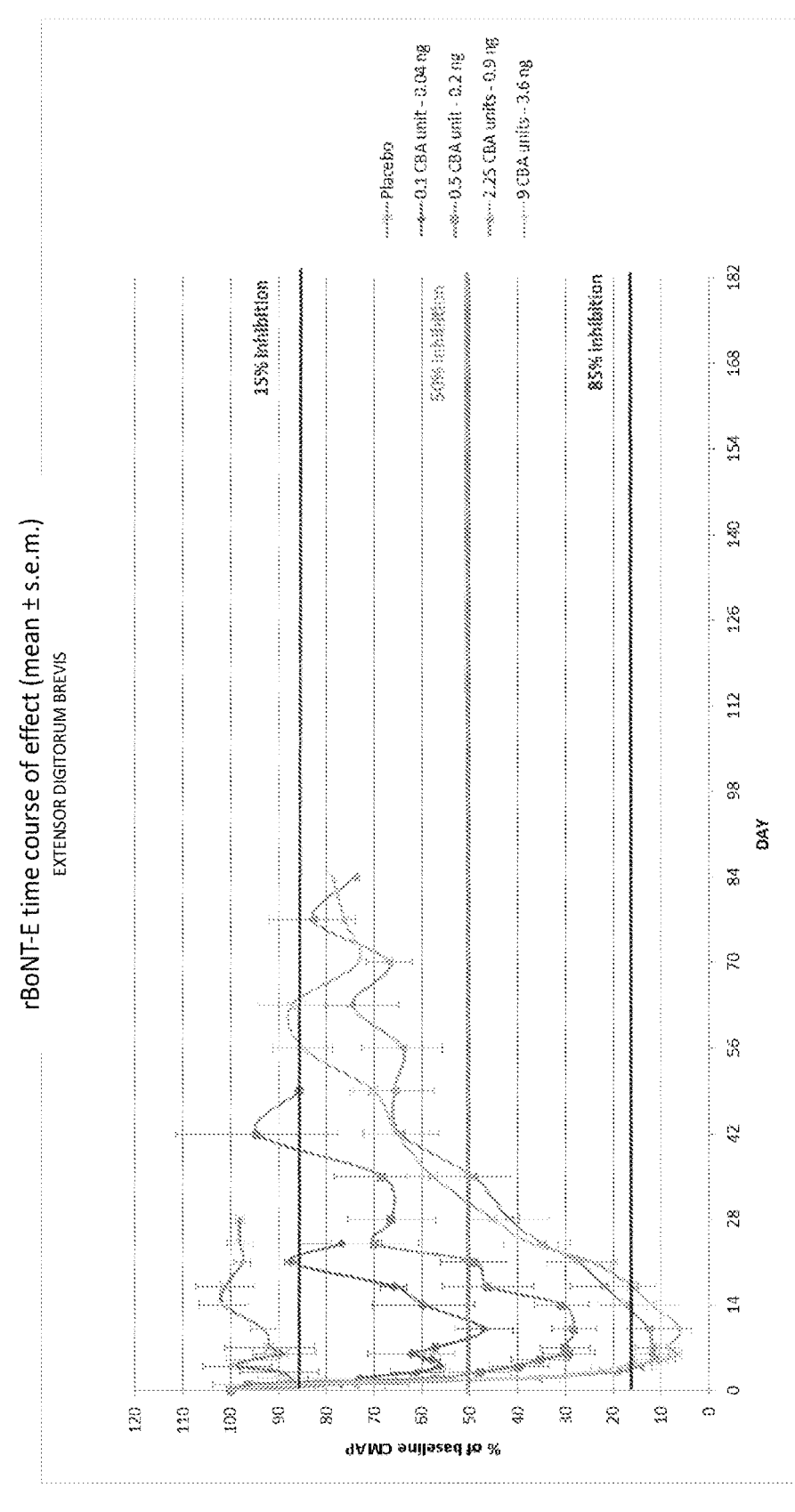
FIG. 5 shows the % of baseline compound muscle action potential (CMAP) of the stimulated extensor digitorum brevis muscle over a 26 week period following administration of different doses of rBoNT/E compared to placebo (mean+/−s.e.m.).

A comparison of FIGS. 4 and 5 shows that for the dose ranges investigated rBoNT-E had a faster onset of effect, greater peak effect and shorter duration of effect.

Example 3

Onset of Action

Figure 6:
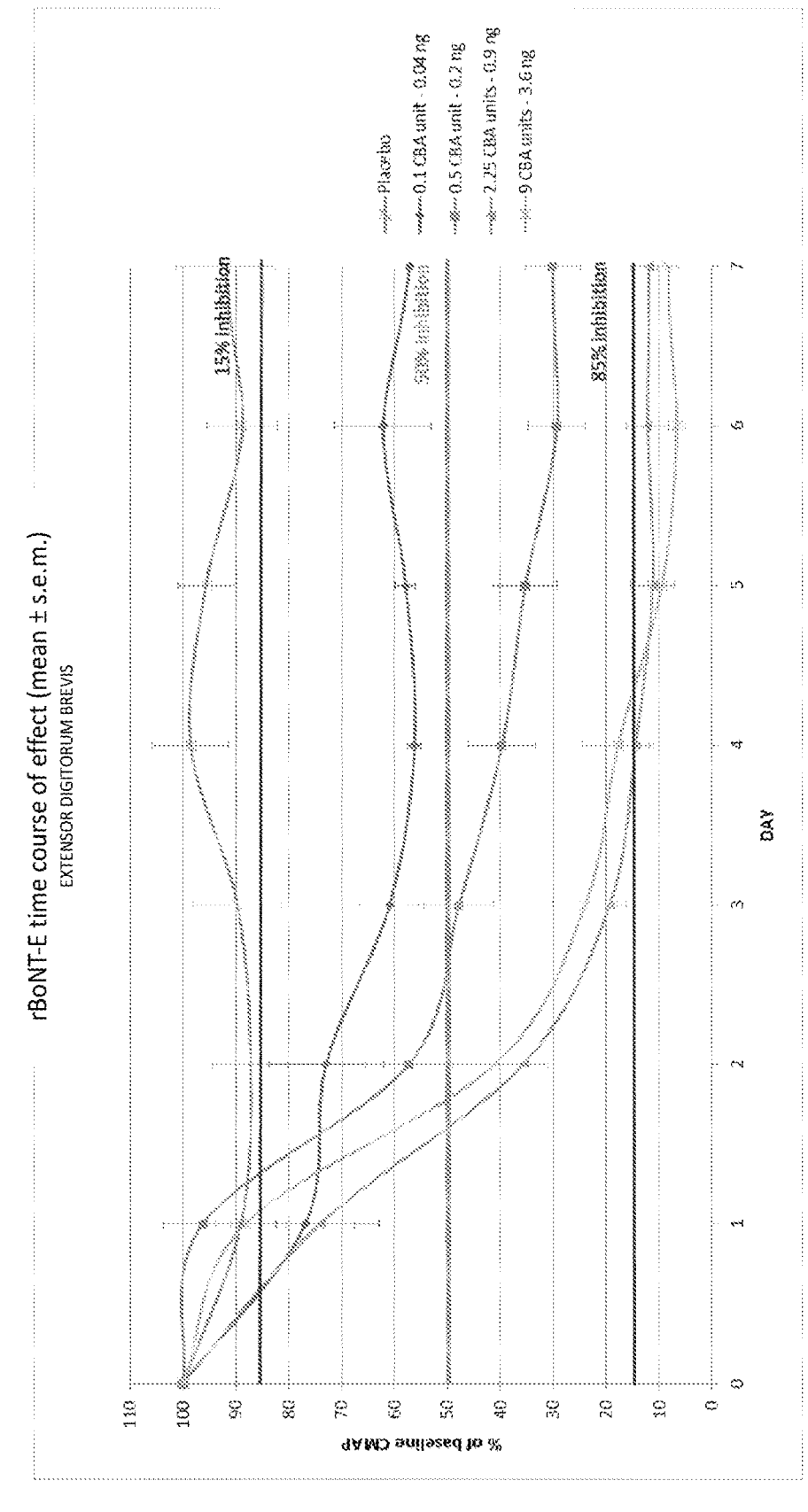
FIG. 6 shows the % of baseline compound muscle action potential (CMAP) of the stimulated extensor digitorum brevis muscle over a 7 day period following administration of different doses of rBoNT/E compared to placebo (mean+/−s.e.m.).
Figure 7:
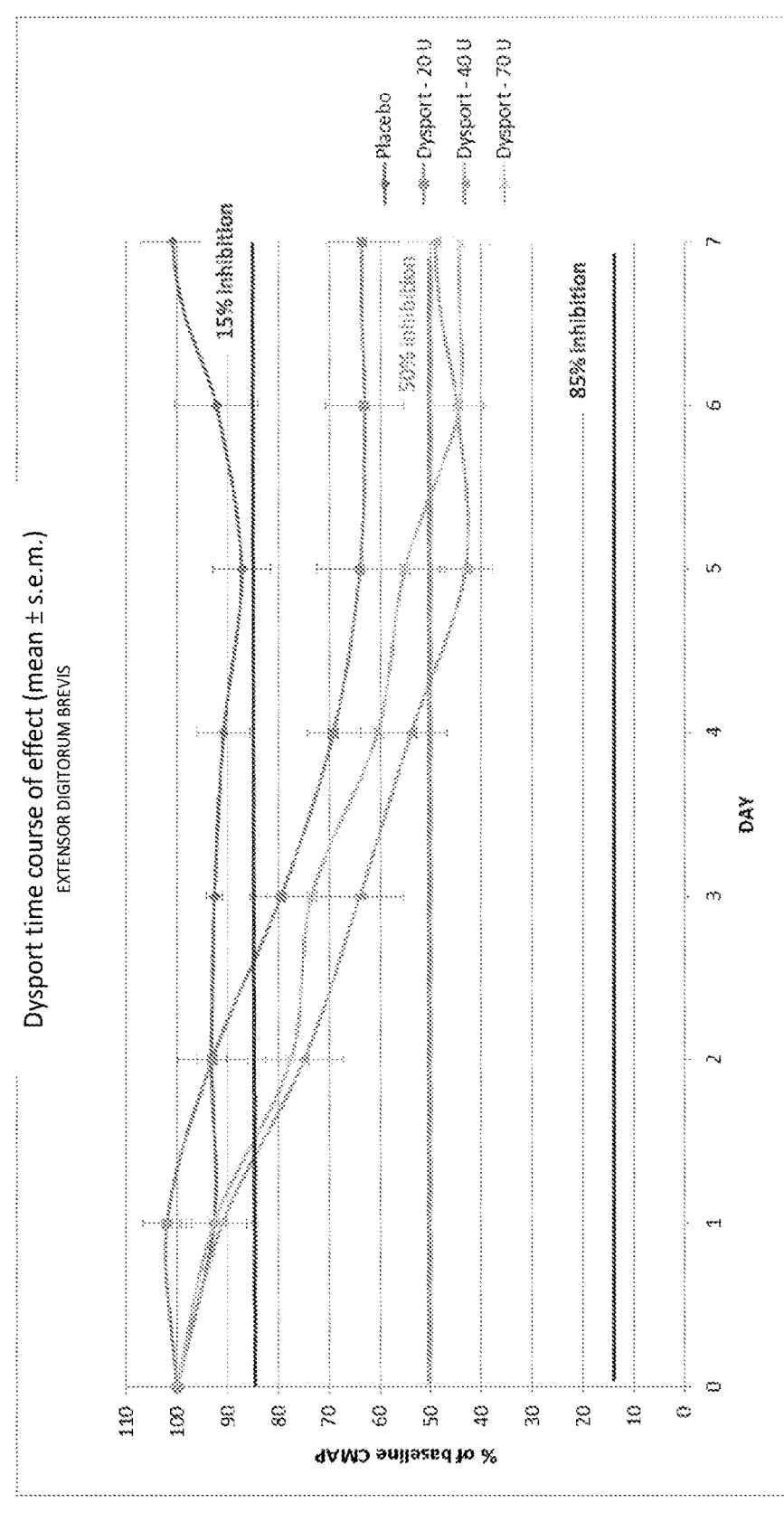
FIG. 7 shows the % of baseline compound muscle action potential (CMAP) of the stimulated extensor digitorum brevis muscle over a 7 day period following administration of different doses of Dysport® compared to placebo (mean+/−s.e.m.).

The time to onset of action (defined as first timepoint where 15% CMAP inhibition recorded) for BoNT/E was fast and consistent in all subjects and all rBoNT-E dose levels investigated. The onset was also found to range between Day 1 (day of BoNT/E administration) and Day 2 versus Day 1 to Day 7 with Dysport®. Results are presented in FIGS. 6 and 7 and values summarised in the tables below.

Table 1 shows data for rBoNT/E.

| Dose Level | 0.1 CBA unit (0.04 ng) n = 3 | 0.5 CBA unit (0.2 ng) n = 6 | 2.25 CBA units (0.9 ng) n = 6 | 9 CBA units (3.6 ng) n = 6 |
|---|---|---|---|---|
| Time to onset (Day) | 1.7 ± 0.6 [1-2] | 1.7 ± 0.5 [1-2] | 1.2 ± 0.4 [1-2] | 1.5 ± 0.5 [1-2] |
| Time to reach maximal inhibition (Day) | 9.0 ± 1.7 [7-10] | 8.8 ± 4.8 [2-14] | 5.8 ±2 .5 [3-10] | 7.8 ± 2.4 [5-10] |
| Maximal inhibition (%) | 53.7 ± 9.1 [43.7-61.6] | 72.3 ± 14.9 [45.1-87.8] | 91.5 ± 7.6 [77.6-100] | 95.8 ± 3.1 [91.6-98.7] |
| Time to recovery (Day) | 21.0 ± 0.0 [21-21] | 37.0 ± 9.3 [24-49] | 57.4 ± 15.2 [42-77] | 54.6 ± 7.7 [42-63] |
| Duration of effect (days) | 19.5 ± 0.7 [19-20] | 35.2 ± 9.6 [22-48] | 56.2 ± 15.1 [41-76] | 53.0 ± 8.0 [40-62] | rBoNT/E was associated with a fast onset of action between Day 1 (day of administration) and Day 2. Time to maximal effect was recorded between Day 2 and Day 14 (at the latest). rBoNT/E was also associated with a short duration of action lasting around 50 days for the two highest tested doses.

Table 2 shows data for Dysport®.

| Dose level | Dysport 20 U (n = 6) | Dysport 46 U (n = 6) | Dysport 70 U (n = 6) |
|---|---|---|---|
| Time to onset (Day) | 3.5 ± 2.1 [1-7] | 2.3 ± 1.0 [1-4] | 2.7 ± 1.9 [1-6] |
| Time to reach maximal inhibition (Day) | 56.5 ± 42.9 [21-133] | 29.3 ± 19.3 [5-56] | 15.3 ± 6.7 [6-24] |
| Maximal inhibition (%) | 52.2 ± 13.3 [36.4-70.6] | 72.5 ± 12.8 [58.4-92.1] | 70.3 ± 7.8 [57.1-77.9] |
| Time to recovery (Day) | >Day 182 [a] | >Day 182 [a] | >Day 182 [a] |

[a] CMAP inhibition did not recovered 15% baseline at the end of the 6-month follow-up period Dysport® exhibited a later onset of action between Day 1 and Day 7 for the dose range investigated, and a duration of action beyond 26-week post-dose.

Example 4

A Comparison of 40 pg rBoNT/E and 20 U Dysport®

Figure 8:
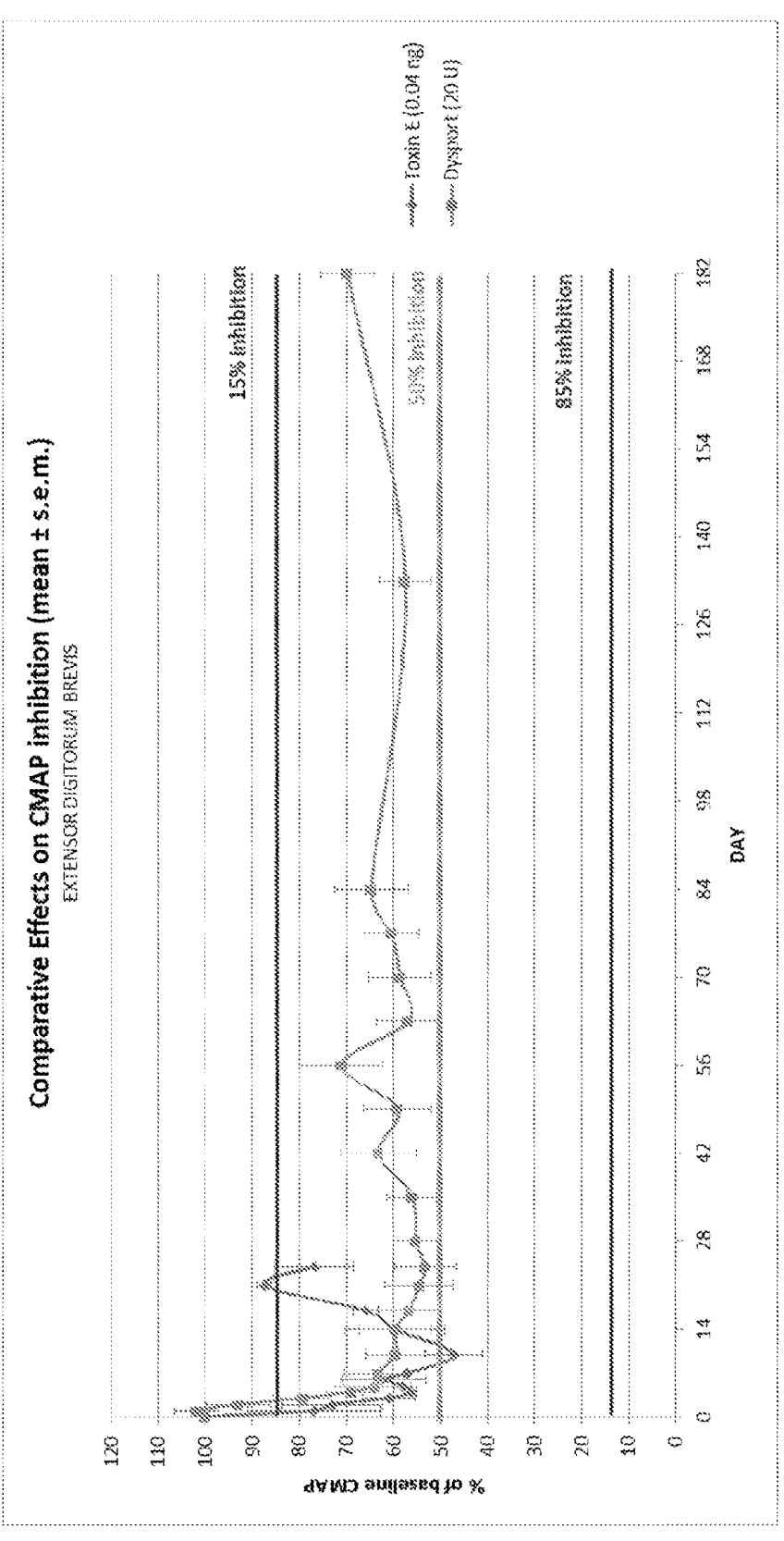
FIG. 8 shows the % of baseline compound muscle action potential (CMAP) of the stimulated extensor digitorum brevis muscle over a 26 week period following administration of 0.04 ng of rBoNT/E or 20 U Dysport® (mean+/−s.e.m.).
Figure 9:
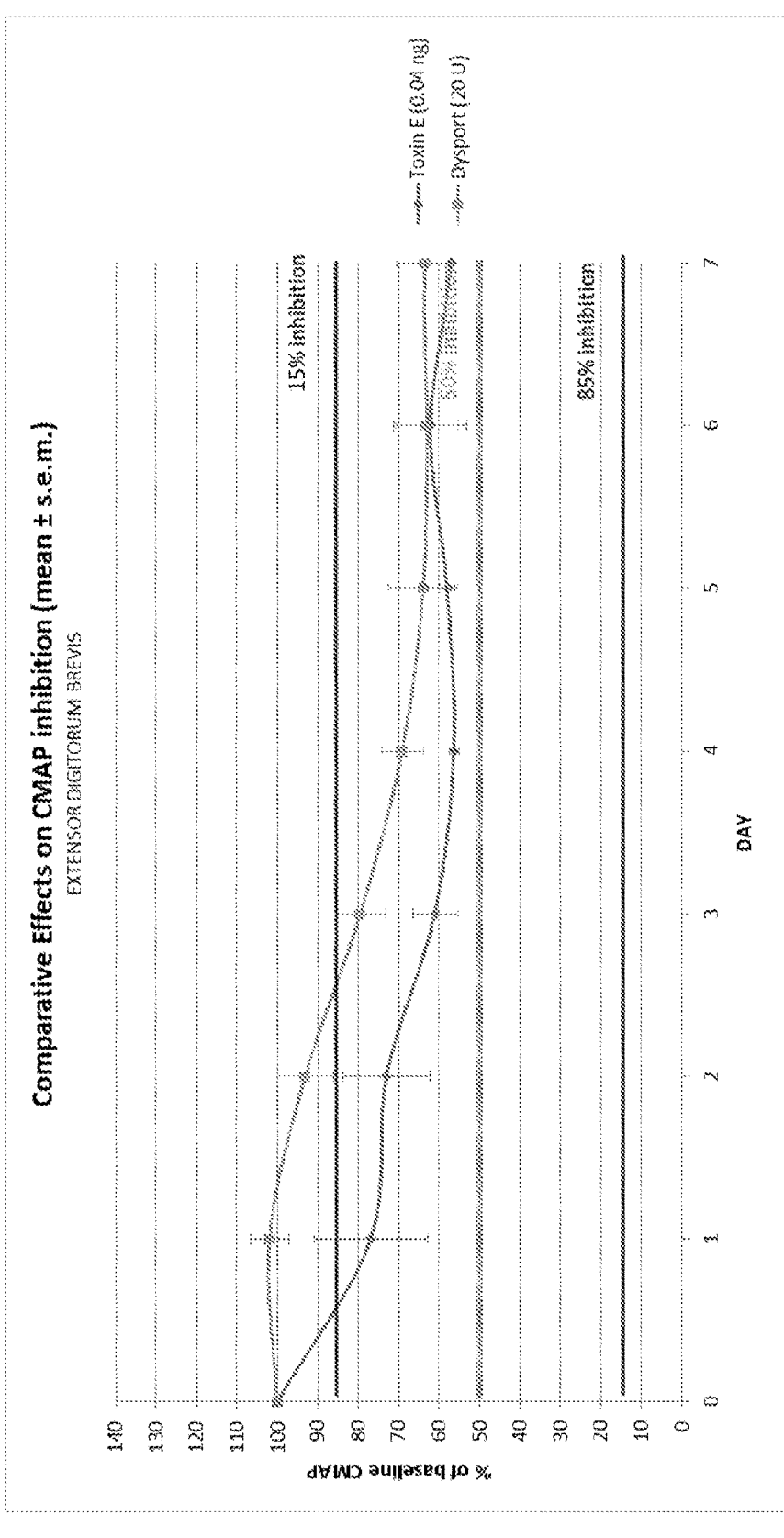
FIG. 9 shows the % of baseline compound muscle action potential (CMAP) of the stimulated extensor digitorum brevis muscle over a 7 day period following administration of 0.04 ng of rBoNT/E or 20 U Dysport® (mean+/−s.e.m.).

FIGS. 8 and 9 show that 40 pg rBoNT-E leads to the same amplitude of effect as 20 U Dysport®. Notably, 20 U Dysport=108 pg neurotoxin (5.38 pg neurotoxin/U).

A comparison of the PD properties are compared in the table below.

Table 3 shows comparative data for rBoNT/E and Dysport®.

| PD parameter | rBoNT-E - 40 pg | Dysport 20 U |
|---|---|---|
| Time to onset | D 1-D 2 | D 1-D 7 |
| Maximal effect | ~50% inhibition on average | ~50% inhibition on average |
| Time to max effect | 9 days on average | 57 days on average |
| Duration of effect | 20 days on average | >6 months on average * |

* about 40 days for 2/6 subjects > 26 weeks for 4/6 subjects

Example 5

A Comparison of 200 pg rBoNT/E and 40 U Dysport®

Figure 10:
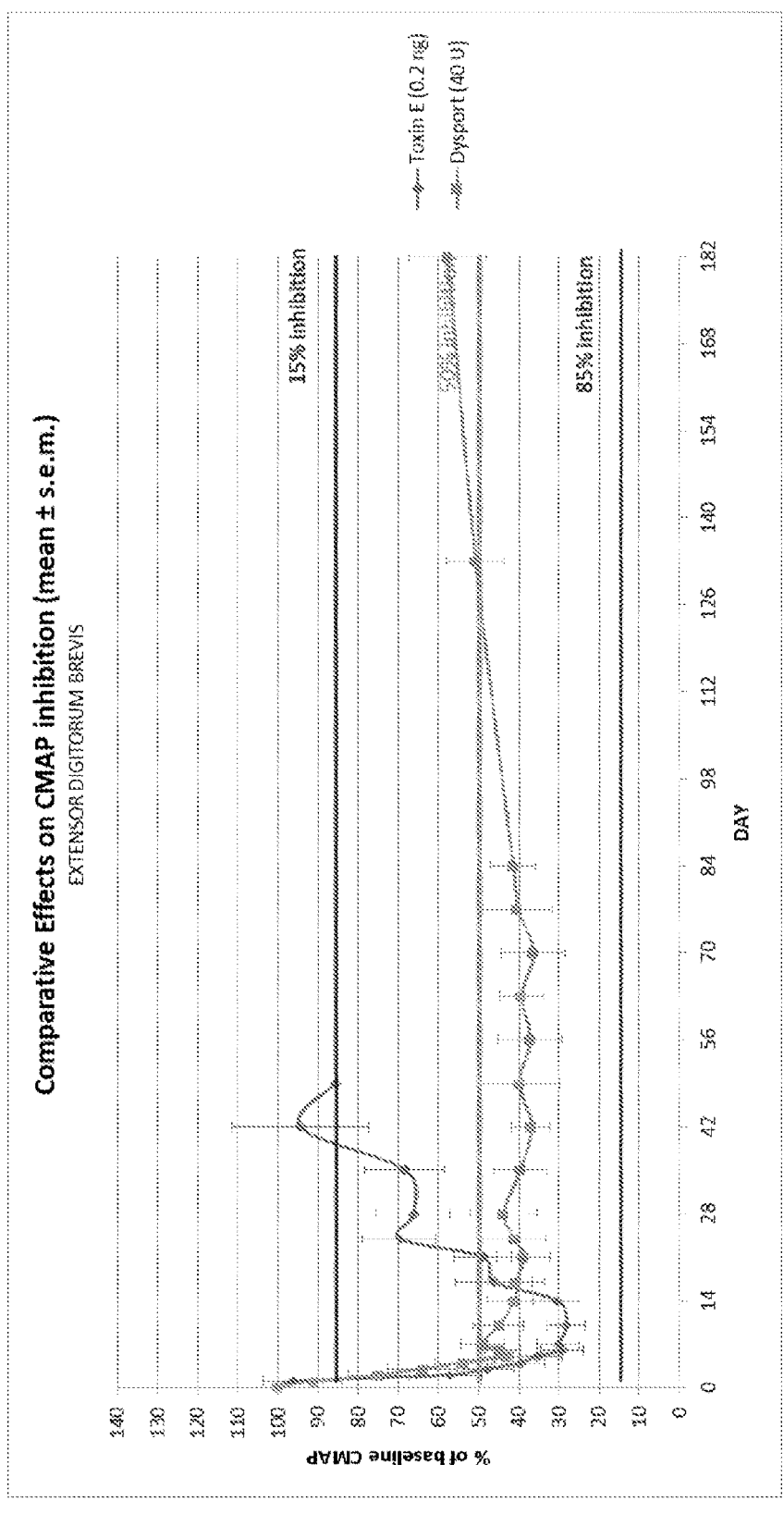
FIG. 10 shows the % of baseline compound muscle action potential (CMAP) of the stimulated extensor digitorum brevis muscle over a 26 week period following administration of 0.2 ng of rBoNT/E or 40 U Dysport® (mean+/−s.e.m.).
Figure 11:
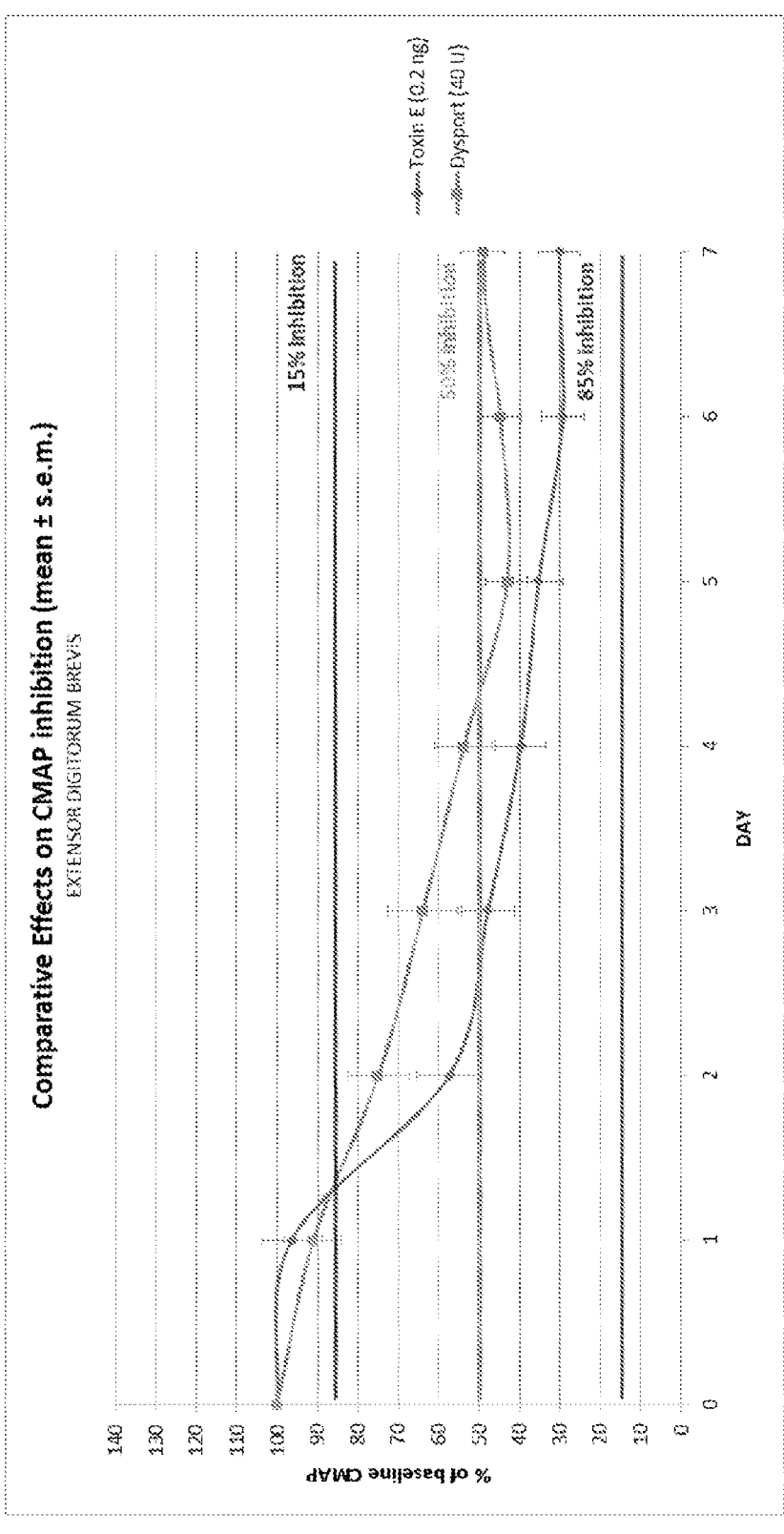
FIG. 11 shows the % of baseline compound muscle action potential (CMAP) of the stimulated extensor digitorum brevis muscle over a 7 day period following administration of 0.2 ng of rBoNT/E or 40 U Dysport® (mean+/−s.e.m.).
Figure 12:
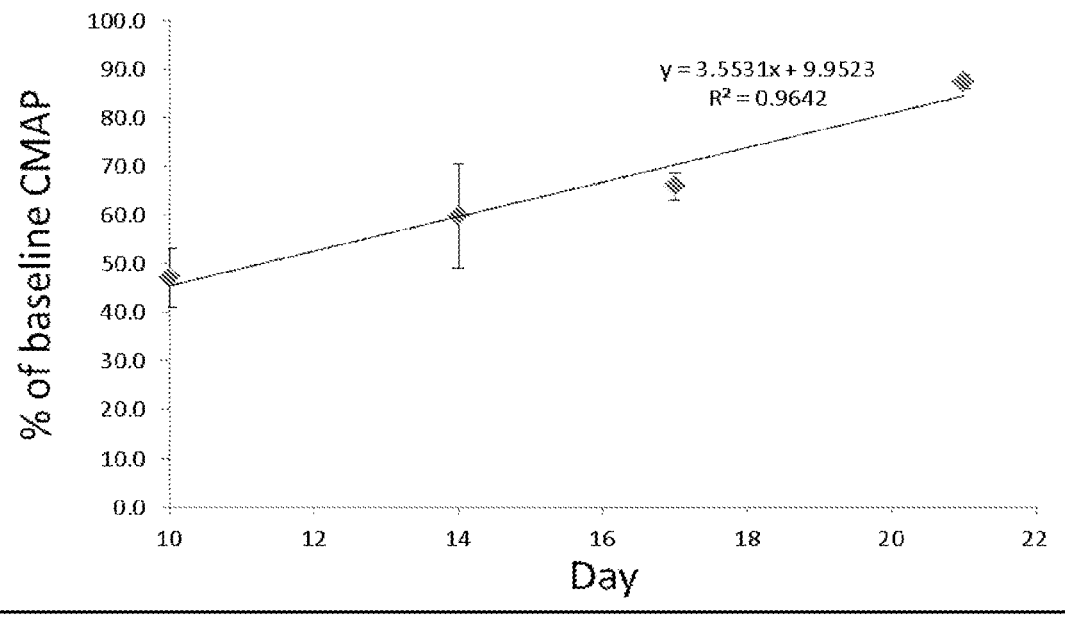
FIG. 12 shows the % of baseline compound muscle action potential (CMAP) of the stimulated extensor digitorum brevis muscle over days 10-21 following administration of 0.04 ng of rBoNT/E (mean+/−s.e.m.). A linear curve has been fit to the CMAP values (Microsoft Excel), which has an R-squared value of 0.9642, and a slope of y=3.5531x+ 9.9523. The CMAP values correspond to those shown for this dose in FIG. 3.
Figure 13:
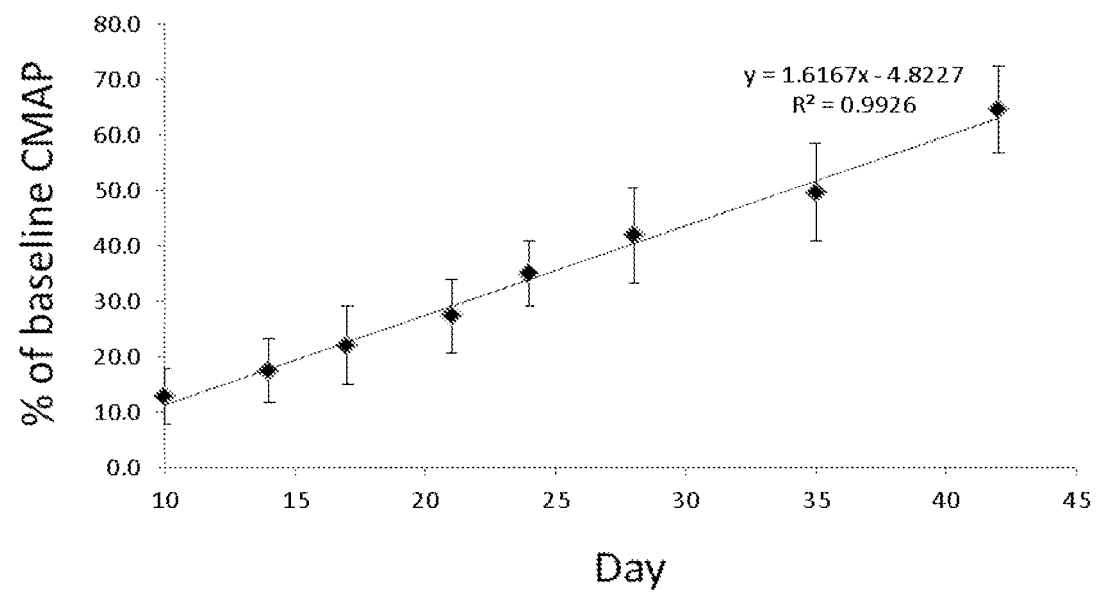
FIG. 13 shows the % of baseline compound muscle action potential (CMAP) of the stimulated extensor digitorum brevis muscle over days 10-42 following administration of 0.9 ng of rBoNT/E (mean+/−s.e.m.). A linear curve has been fit to the CMAP values (Microsoft Excel), which has an R-squared value of 0.9926, and a slope of y=1.6167x +4.8227. The CMAP values correspond to those shown for this dose in FIG. 3.
Figure 14:
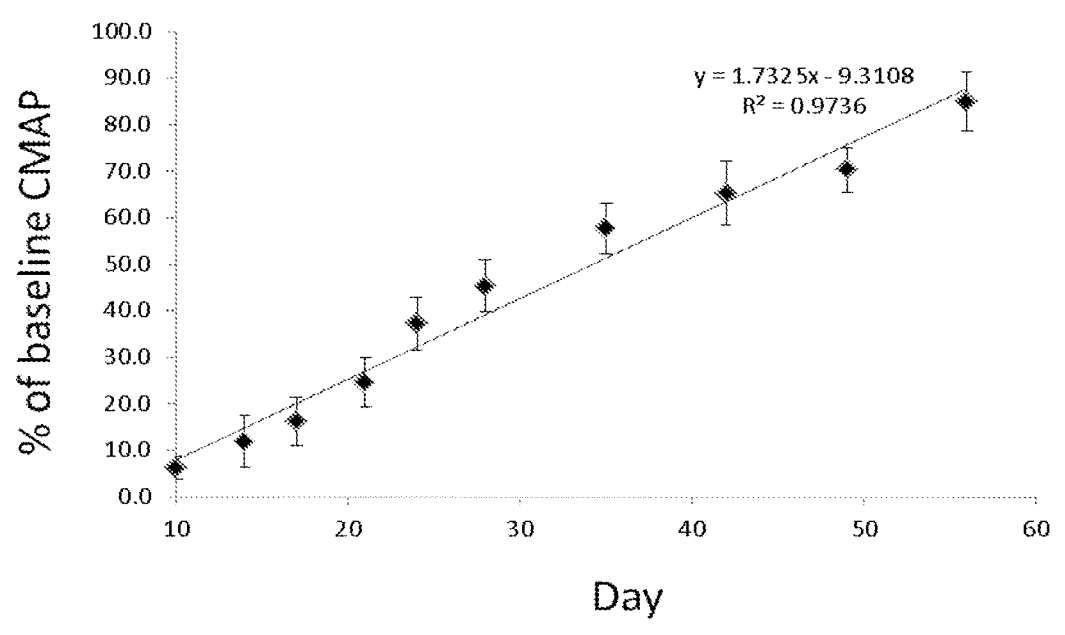
FIG. 14 shows the % of baseline compound muscle action potential (CMAP) of the stimulated extensor digitorum brevis muscle over days 10-56 following administration of 3.6 ng of rBoNT/E (mean+/−s.e.m.). A linear curve has been fit to the CMAP values (Microsoft Excel), which has an R-squared value of 0.9736, and a slope of y=1.7325x −9.3108. The CMAP values correspond to those shown for this dose in FIG. 3.

FIGS. 10 and 11 show that 200 pg rBoNT-E leads to the same amplitude of effect as 40 U Dysport®. A comparison of the PD properties are compared in the table below.

Table 4 shows comparative data for rBoNT/E and Dysport®.

| PD parameter | rBoNT-E - 200 pg | Dysport 40 U |
|---|---|---|
| Time to onset | D 1-D 2 | D 1-D 4 |
| Maximal effect | ~70% inhibition on average | ~70% inhibition on average |
| Time to max effect | 9 days on average | 29 days on average |
| Duration of effect | 35 days on average | >6 months on average |

In conclusion, BoNT/E exhibited:

a good overall safety profile for single intramuscular doses of rBoNT-E up to 3.6 ng in healthy volunteers (normal muscle);

no local diffusion to adjacent muscles (AH and ADQ);

a fast onset of action irrespective of the investigated dose;

a dose dependent amplitude of effect with maximal effect reached from 0.9 ng;

a maximal effect reached within approximately one week; and a similar PD profile for the two highest tested doses associated with a duration of effect of approximately 50 days.

In contrast, inhibition of the CMAP was still observed at the end of the 26-week (6 months) recording period for Dysport®.

In respect of the amplitude of maximal effect:

20 U Dysport compares to 0.04 ng rBoNT-E; and 40-70 U Dysport compares to 0.2 ng rBoNT-E

Example 6

Treatment of Upper Facial Lines

A subject with severe glabellar lines (grade 3 according to the Facial Wrinkle Scale (FWS), where 0=none and 3=severe) is presented. A dose of at least 0.1 ng (per injection site) of rBoNT/E is injected intramuscularly at five sites (sequentially, such that each muscle is injected at substantially the same time): one in the procerus muscle, and two in each corrugator supercilii muscle.

The severity of glabellar lines in the subject is assessed at 7 days (after administration) using the FWS, and a grade of 0 is determined (therefore, the rBoNT/E is demonstrated to have a fast onset of action for treating upper facial lines).

The severity of glabellar lines in the subject is assessed at 35 days (after administration) using the FWS, and a grade of 2 (moderate) is determined.

The severity of glabellar lines in the subject is assessed at 56 days (after administration) using the FWS, and a grade of 3 (severe) is determined (therefore, the rBoNT/E is demonstrated to have a short duration of effect for treating upper facial lines).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for treating skin wrinkles in a subject in need thereof, the method comprising administering to the subject a total dose of BoNT/E of from about 0.03 ng to about 0.5 ng, wherein the BoNT/E is in a non-complexed form.

2. The method of claim 1, wherein the BoNT/E is recombinant BONT/E.

3. The method of claim 2, wherein: (a) at least 40% inhibition of neurotransmitter secretion from a target cell or tissue is achieved within 13 days following administration of the BoNT/E to the subject; and (b) no more than 15% inhibition of neurotransmitter secretion from the target cell or tissue occurs between 21 days and 100 days following administration of the BoNT/E to the subject.

4. The method of claim 1, wherein the decrease in percent inhibition of neurotransmitter secretion following maximum inhibition of neurotransmitter secretion is substantially linear.

5. The method of claim 1, wherein at least 40% inhibition of neurotransmitter secretion from the target cell or tissue is achieved within 10 days following administration of the BoNT/E to the subject.

6. The method of claim 1, wherein the percent inhibition of neurotransmitter secretion from the target cell or tissue is reduced to 15% or less within 80 days following administration of the BoNT/E to the subject.

7. The method of claim 1, wherein at least 15% inhibition of neurotransmitter secretion is achieved for 5 to 100 days.

8. The method of claim 1, wherein 40% to 60% inhibition of neurotransmitter secretion from a target cell or tissue is achieved within 13 days following administration of the BoNT/E to the subject.

9. The method of claim 1, wherein 40% to 60% inhibition of neurotransmitter secretion from a target cell or tissue is achieved within 11 days following administration of the BoNT/E to the subject.

10. The method of claim 1, wherein: (a) maximal inhibition of neurotransmitter secretion from a target cell or tissue is achieved within 13 days following administration of the BoNT/E to the subject; and (b) following maximal inhibition, the percent inhibition of neurotransmitter secretion reduces 1 to 10% per day.

11. The method of claim 1, wherein: (a) maximal inhibition of neurotransmitter secretion from a target cell or tissue is achieved within 10 days following administration of the BoNT/E to the subject; and (b) the percent inhibition is reduced 1% to 3% per day 10 to 24 days following administration of the BoNT/E to the subject.

12. The method of claim 2, wherein the percent inhibition of neurotransmitter secretion from a target cell or tissue is measured by electrophysiology.

13. The method of claim 1, wherein the BoNT/E comprises an amino acid sequence: (a) having at least 95% sequence identity to SEQ ID NO:3; and (b) includes one or more of the following amino acids at the specified positions numbered from the N-terminal methionine: (i) glycine at position 177; (ii) serine at position 198; (iii) alanine at position 340; (iv) leucine at position 773; (v) leucine at position 963; (vi) glutamine at position 964; (vii) alanine at position 967; and (viii) asparagine at position 1195.

14. The method of claim 1, wherein the BoNT/E comprises an amino acid sequence: (a) having at least 98% sequence identity to SEQ ID NO:3; and (b) includes one or more of the following amino acids at the specified positions numbered from: (i) glycine at position 177; (ii) serine at position 198; (iii) alanine at position 340; (iv) leucine at position 773; (v) leucine at position 963; (vi) glutamine at position 964; (vii) alanine at position 967; and (viii) asparagine at position 1195.

15. The method of claim 1, wherein the BoNT/E comprises an amino acid sequence: (a) having at least 99% sequence identity to SEQ ID NO:3; and (b) includes one or more of the following amino acids at the specified positions numbered from the N-terminal methionine: (i) glycine at position 177; (ii) serine at position 198; (iii) alanine at position 340; (iv) leucine at position 773; (v) leucine at position 963; (vi) glutamine at position 964; (vii) alanine at position 967; and (viii) asparagine at position 1195.

16. The method of claim 1, wherein the BoNT/E comprises the amino acid sequence of SEQ ID NO:3 or one that: (a) differs therefrom by 30 or fewer conservative amino acid substitutions; and (b) includes one or more of the following amino acids at the specified positions numbered from the N-terminal methionine: (i) glycine at position 177; (ii) serine at position 198; (iii) alanine at position 340; (iv) leucine at position 773; (v) leucine at position 963; (vi) glutamine at position 964; (vii) alanine at position 967; and (viii) asparagine at position 1195.

17. The method of claim 1, wherein the BoNT/E comprises the amino acid sequence of SEQ ID NO: 2.

18. The method of claim 1, comprising administering to the subject a total dose of BoNT/E in a range from 0.1 ng to 0.5 ng.

19. The method of claim 1, comprising administering to the subject a total dose of BoNT/E in a range from 0.03 ng to 0.2 ng.

20. The method of claim 1, comprising administering to the subject a total dose of BoNT/E in a range from 0.04 ng to 0.15 ng.

21. The method of claim 1, comprising administering to the subject a total dose of BoNT/E in a range from 0.03 ng to 0.24 ng.

22. The method of claim 1, for treating upper facial lines, lateral canthal lines and/or frontalis lines.

23. The method of claim 2, for treating glabellar lines.

24. The method of claim 1, wherein the total dose of BoNT/E administered to the subject is about 0.5 ng.

*    *    *    *    *